United States Patent [19]

Wolf

[11] Patent Number: 4,602,940

[45] Date of Patent: Jul. 29, 1986

[54] HERBICIDAL SULFONAMIDES

[75] Inventor: Anthony D. Wolf, Elkton, Md.

[73] Assignee: E. I. Du Pont de Nemours and Company, Wilmington, Del.

[21] Appl. No.: 736,212

[22] Filed: May 20, 1985

Related U.S. Application Data

[60] Division of Ser. No. 630,222, Jul. 12, 1984, Pat. No. 4,534,790, which is a division of Ser. No. 428,806, Oct. 7, 1982, Pat. No. 4,465,505, which is a continuation-in-part of Ser. No. 337,932, Jan. 7, 1982, abandoned.

[51] Int. Cl.$^4$ .................. C07D 413/12; A01N 47/36

[52] U.S. Cl. .................................. 71/92; 71/90; 544/54; 544/96; 544/253; 544/278; 544/296; 544/321; 544/324; 544/331; 548/146; 548/183; 548/187; 548/204; 548/232; 548/236; 548/237; 548/268

[58] Field of Search ............... 544/321, 324, 331, 253, 544/278, 296, 96, 54; 71/90, 92; 548/268, 204, 183, 187, 146, 232, 236, 237

[56] References Cited

U.S. PATENT DOCUMENTS 4,370,480  1/1983  Levitt et al. .................. 544/320

Primary Examiner—Robert Gerstl

[57] ABSTRACT

This invention relates to ortho-heterocyclic benzene sulfonylureas which are useful as herbicides and growth regulants.

31 Claims, No Drawings

HERBICIDAL SULFONAMIDES

RELATED APPLICATION

This is a division of application Ser. No. 630,222 filed July 12, 1984, U.S. Pat. No. 4,534,790, which is a division of Ser. No. 428,806 filed Oct. 7, 1982 now U.S. Pat. No. 4,465,505 which is a continuation-in-part of my copendend application U.S. Ser. No. 337,932 filed Jan. 7, 1982, now abandoned.

BACKGROUND OF THE INVENTION

This invention relates to ortho-heterocyclic sulfonylureas and in particular, to their use as agricultural chemicals such as herbicides and growth regulants.

U.S. Pat. No. 4,127,405 teaches compounds which are useful for controlling weeds in wheat having the formula:

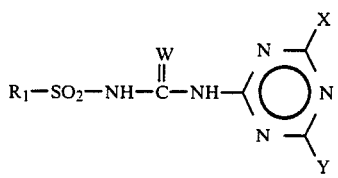

wherein $R_1$ is

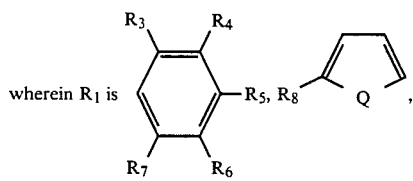

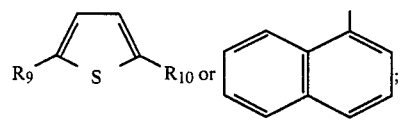

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

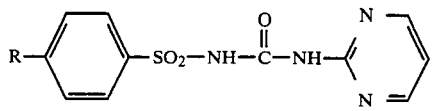

wherein

R=H, halogen, $CF_3$ or alkyl.

Logemann et al., Chem. Ab., 53, 18052g (1959), disclose a number of sulfonamides, including uracil derivatives and those having the formula:

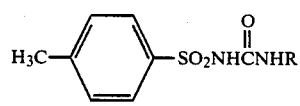

wherein

R is butyl, phenyl or

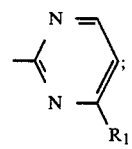

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

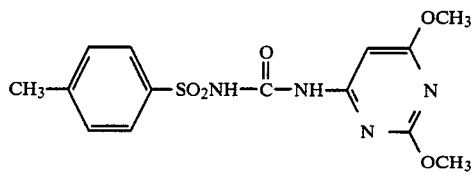

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

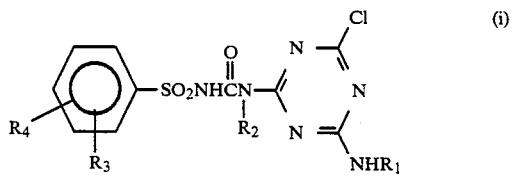

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in *J. Drug. Res.* 6, 123 (1974),

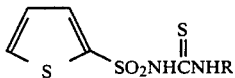
(ii)

wherein
R is pyridyl.

European Patent Application No. 7687, discloses herbicidal sulfonylureas which contain an o-carboalkoxybenzene moiety.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to compounds of Formula I, to agriculturally suitable compositions containing them, and to their use as general and/or selective pre-emergence and/or post-emergence herbicides, and as plant growth regulants.

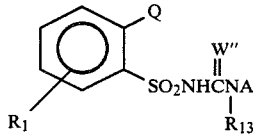
I where
Q is

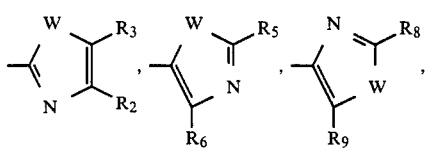

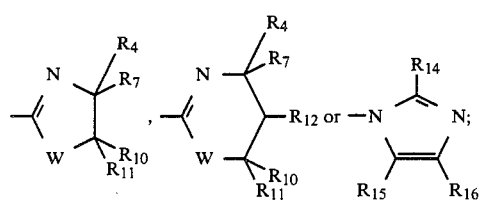

$W'''$ is O or S;
W is O, S, or NR;
R is H or $C_1$–$C_4$ alkyl;

$R_1$ is H, F, Cl, Br, $CH_3$, $CF_3$ or $OCH_3$;
$R_2$ is H, $CH_3$, $C_2H_5$, $OCH_3$, $OC_2H_5$, $SCH_3$, Cl or Br;
$R_3$ is H, $CH_3$, $C_2H_5$, $OCH_3$, $OC_2H_5$, $SCH_3$, Cl or Br;
$R_5$ is H, $CH_3$, $C_2H_5$, $OCH_3$, $OC_2H_5$, $SCH_3$, Cl or Br;
$R_6$ is H, $CH_3$ or $C_2H_5$;
$R_8$ is H, $CH_3$, $C_2H_5$, $OCH_3$, $OC_2H_5$, $SCH_3$, Cl or Br;
$R_9$ is H, $CH_3$ or $C_2H_5$;
$R_4$, $R_7$, $R_{10}$ and $R_{11}$ are independently H or $C_1$–$C_4$ alkyl;
$R_{12}$ is H or $CH_3$;
$R_{13}$ is H or $CH_3$;
$R_{14}$ is H, $CH_3$, $C_2H_5$, Cl, Br, $CH_3O$, $C_2H_5O$ or $CH_3S$;
$R_{15}$ is H, $CH_3$ or $C_2H_5$;
$R_{16}$ is H, $CH_3$ or $C_2H_5$;
A is

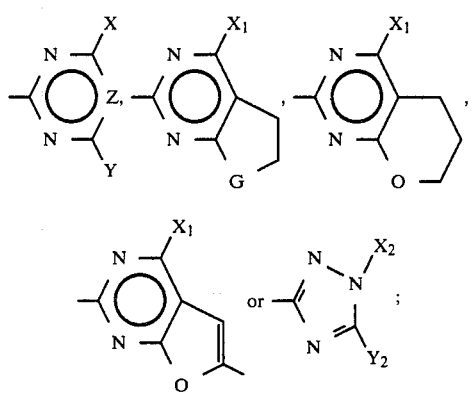

X is $CH_3$, $OCH_3$ or Cl;
Y is $CH_3$, $C_2H_5$, $CH_2OCH_3$, $OCH_3$, $OC_2H_5$, $CH(OCH_3)_2$, $NH_2$, $NHCH_3$, $N(CH_3)_2$, $OCH_2CH_2OCH_3$, $OCH_2CF_3$, $CF_3$, $SCH_3$ or

Z is CH or N;
$X_1$ is $CH_3$, $OCH_3$ or Cl;
G is O or $CH_2$;
$X_2$ is $C_1$–$C_3$ alkyl or $CH_2CF_3$;
$Y_2$ is $CH_3O$, $C_2H_5O$, $CH_3S$ or $C_2H_5S$;
and their agriculturally suitable salts; provided that
(a) when $R_8$ is other than H, $CH_3$, $C_2H_5$ or $CH_3S$, then W is S or O;
(b) the total number of carbon atoms of $R_4$, $R_7$, $R_{10}$ and $R_{11}$ is less than or equal to 4;
(c) when X is Cl, then Z is CH and Y is $OCH_3$, $OC_2H_5$, $NH_2$, $NHCH_3$ or $N(CH_3)_2$;
(d) when Q is

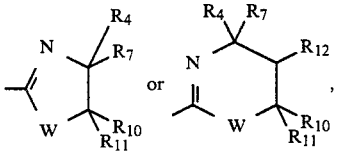

then $R_{13}$ is H, R is other than H, X is Cl or $OCH_3$ and Y is $OCH_3$ or $OC_2H_5$; and
(e) when $W'''$ is S, then $R_{13}$ is H;
Q is

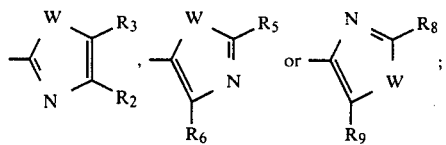

A is

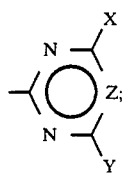

and
Y is $CH_3$, $OCH_3$, $C_2H_5$, $OC_2H_5$, $CH_2OCH_3$, $CH(OCH_3)_2$ or

Preferred for their higher herbicidal activity and/or more favorable ease of synthesis are:
(1) Compounds of Formula I where
R is $CH_3$ or $C_2H_5$;
$R_2$, $R_3$, $R_5$, $R_6$, $R_8$, $R_9$, $R_{14}$, $R_{15}$ and $R_{16}$ are independently H, $CH_3$ or $C_2H_5$;
$R_4$, $R_7$, $R_{10}$ and $R_{11}$ are independently H or $CH_3$; and
W'' is O;
(2) Compounds of the Preferred 1 where $R_1$ and $R_{13}$ are H;
(3) Compounds of Preferred (2) where
Y is $CH_3$, $OCH_3$, $OC_2H_5$, $CH_2OCH_3$ or

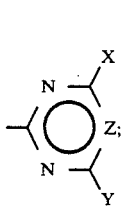

and
A is

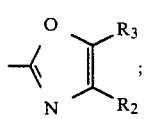

(4) Compounds of Preferred (3) where Q is

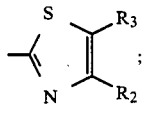

(5) Compounds of Preferred (3) where Q is (6) Compounds of Preferred (3) where Q is

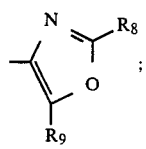

(7) Compounds of Preferred (3) where Q is

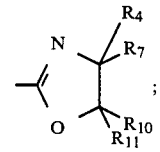

(8) Compounds of Preferred (3) where Q is

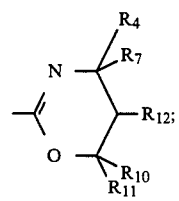

(9) Compounds of Preferred (3) where Q is

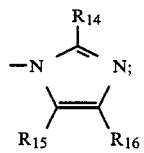

(10) Compounds of Preferred (3) where Q is

(11) Compounds of Preferred (3) where Q is

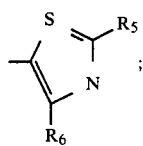

(12) Compounds of Preferred (3) where Q is

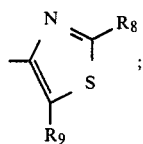

(13) Compounds of Preferred (3) where Q is

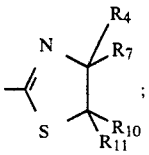

(14) Compounds of Preferred (3) where Q is

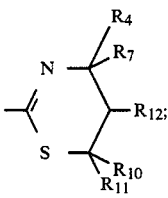

(15) Compounds of Preferred (3) where Q is

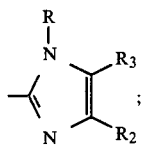

(16) Compounds of Preferred (3) where Q is

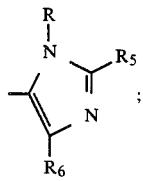

(17) Compounds of Preferred (3) where Q is

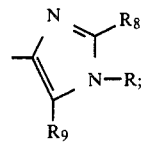

(18) Compounds of Preferred (3) where Q is

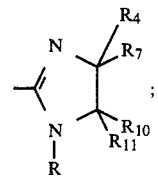

and
(19) Compounds of Preferred (3) where Q is

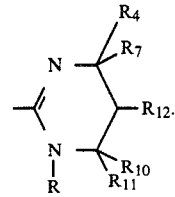

Specifically Preferred are

N-[(4,6-dimethoxypyrimidin-2-yl)aminocarbonyl]-2-(1-methyl-1H-imidazol-2-yl)benzenesulfonamide;
N-[(4,6-dimethylpyrimidin-2-yl)aminocarbonyl]-2-(1-methyl-1H-imidazol-2-yl)benzenesulfonamide;
N-[(4-methoxy-6-methylpyrimidin-2-yl)aminocarbonyl]-2-(1-methyl-1H-imidazol-2-yl)benzenesulfonamide;
N-[(4,6-dimethoxypyrimidin-2-yl)aminocarbonyl]-2-(oxazol-2-yl)benzenesulfonamide;
N-[(4,6-dimethylpyrimidin-2-yl)aminocarbonyl]-2-(oxazol-2-yl)benzenesulfonamide;
N-[(4-methoxy-6-methylpyrimidin-2-yl)aminocarbonyl]-2-(oxazol-2-yl)benzenesulfonamide;
N-[(4,6-dimethoxy-1,3,5-triazin-2-yl)aminocarbonyl]-2-(oxazol-2-yl)benzenesulfonamide;
N-[(4,6-dimethyl-1,3,5-triazin-2-yl)aminocarbonyl]-2-(oxazol-2-yl)benzenesulfonamide;
N-[(4-methoxy-6-methyl-1,3,5-triazin-2-yl)aminocarbonyl]-2-(oxazol-2-yl)benzenesulfonamide; and
2-(4,5-dihydro-5,5-dimethyloxazol-2-yl)-N-[(4,6-dimethoxy-1,3,5-triazin-2-yl)aminocarbonyl]benzenesulfonamide.

SYNTHESIS—OXAZOLES

Compounds of Formula Ia in which Q is other than

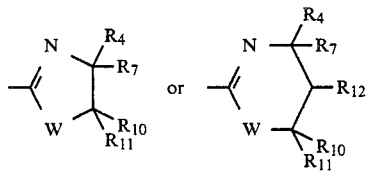

and W''' is O can be prepared by the procedure of Equation 1 in which sulfonamides (1) are reacted with a carbamate (2) in the presence of an equimolar amount of trimethylaluminum. Further details of this reaction and the preparation of carbamates (2) can be found in U.S. Ser. No. 337,934, filed Jan. 7, 1982 and now abandoned.

EQUATION 1

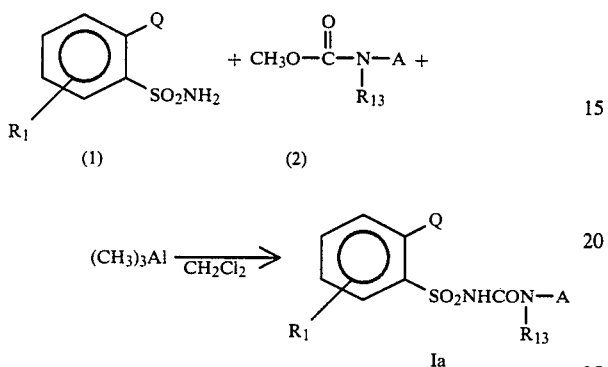

Compounds of Formula I in which Q is other than

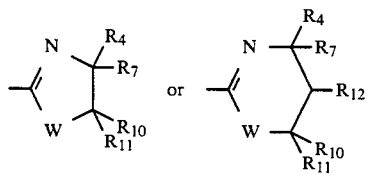

and W''' is O are also prepared by the procedure of Equation 1a.

Equation 1a

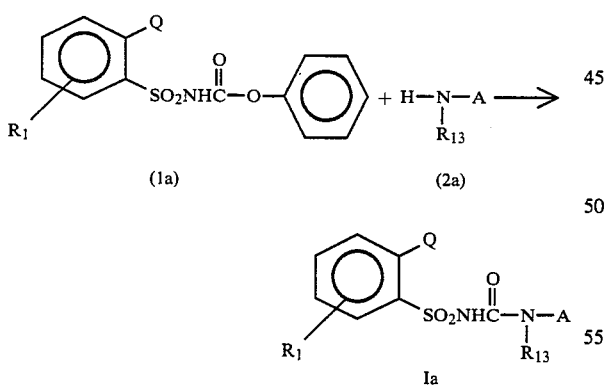

Details of this procedure are described in European Patent Application No. 44809 in which a carbamate (1a) is reacted with an amine (2a) to yield the desired sulfonylureas Ia.

Compounds of Formula I in which $R_{13}$ is H and X is Cl or $OCH_3$ and Y is $OCH_3$ or $OC_2H_5$ are also prepared as shown in Equations 2, 3 and 4. Details of these reactions are described in unexamined European Patent No. 30-140.

Equation 2

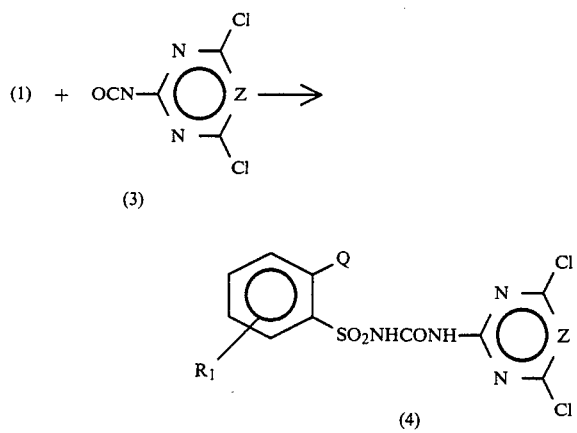

Equation 3

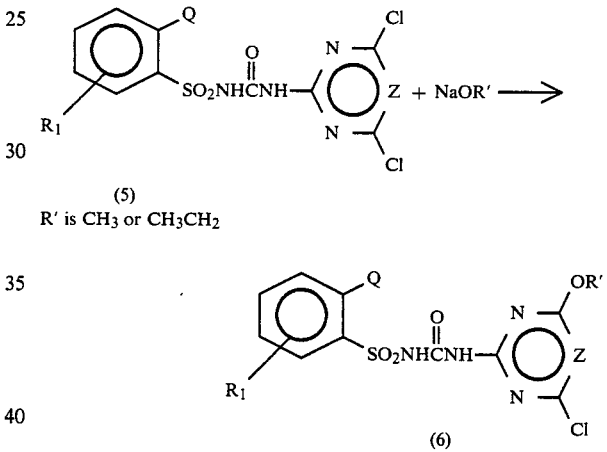

(5)
R' is $CH_3$ or $CH_3CH_2$

Equation 4

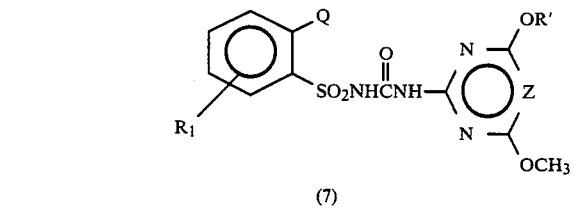

Some of the compounds of Formula I where

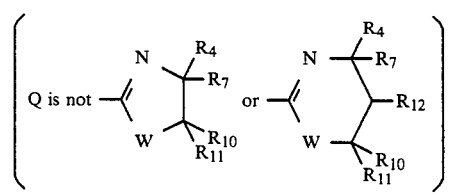

may be prepared as described in Equation 5 in which a heterocyclicamine (9) is reacted with the appropriate sulfonyl isocyanate (8).

Equation 5

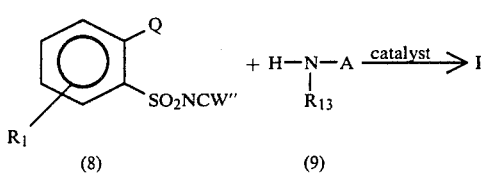

The preparation of heterocyclicamines (9) and sulfonyl isocyanates (8) can be found in U.S. Pat. No. 4,169,719, U.S. Pat. No. 4,127,405, EP Publication 15,683, EP Publication 46,677 and U.S. Patent Application Ser. No. 382,711, along with details of the procedures of Equation 5.

Compounds of Formula I in which W″ is S, A is

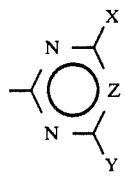

and $R_{13}$ is H are prepared by the procedure of Equation 5a in which a sulfonamide of Formula Ia is reacted with a heterocyclicisothiocyanate of Formula 9a.

Equation 5a

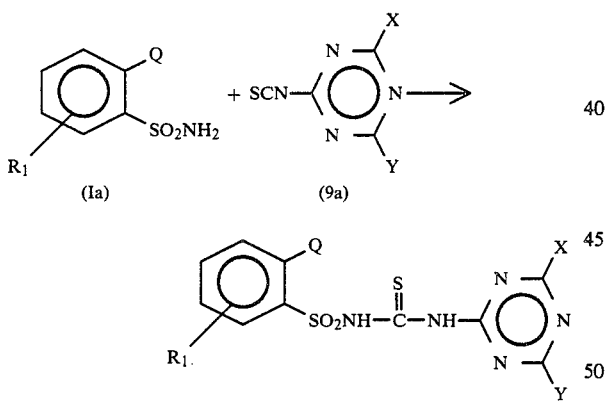

Details of this procedure are described in EPO Publication No. 35,893.

Sulfonamides (Ia) in which R is other than H and Q is other than

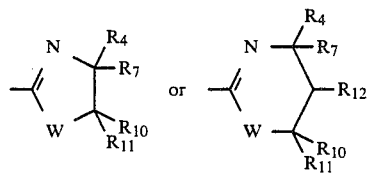

are prepared from the corresponding amines which in turn are prepared from the corresponding aromatic nitro compounds as described in Equations 6, 7 and 8.

Equation 6

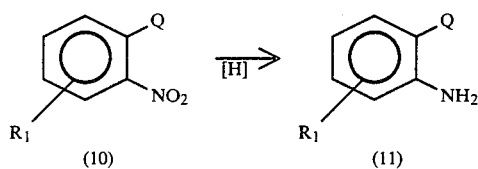

Equation 7

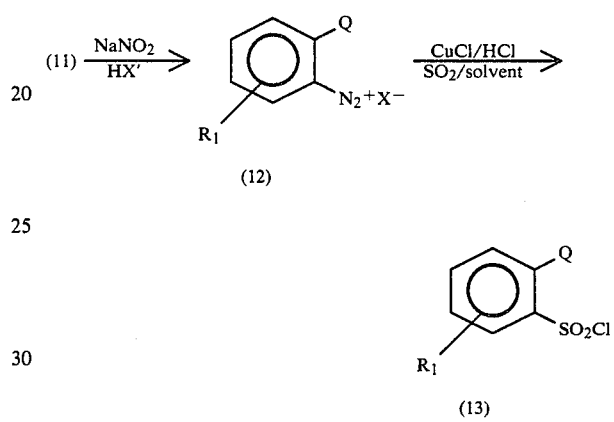

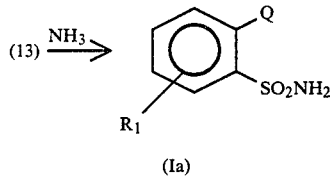

Equation 8

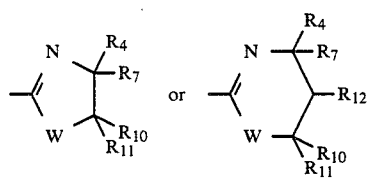

The reduction of aromatic nitro compounds to aromatic amines (Equation 6) is well known in the art.

The preparation of sulfonamides from aromatic amines by the procedures of Equations 7 and 8 is also well known in the art. For details see U.S. Pat. No. 4,127,405 and references therein.

Sulfonamides (Ia) in which Q is

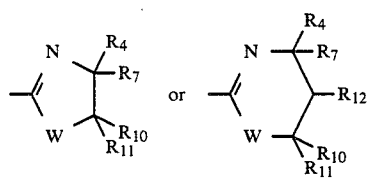

are best prepared by the procedure of Equations 9 and 10.

Equation 9

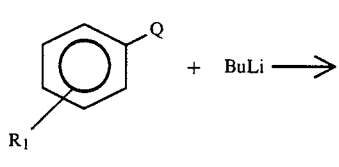

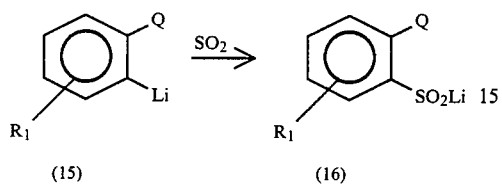

Equation 10

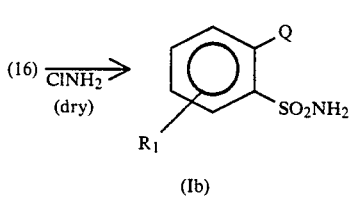

The preparation of sulfinic acid salts (16) by the procedure of Equation 9 is well known in the art. See U.S. Pat. No. 4,127,405 and *Organic Reactions*, Vol. 26, 1979, J. Wiley and Sons, Inc., N.Y. Sulfonamides (Ib) are best prepared by treatment of sulfinic acid salts with chloramine. In this procedure an ethereal solution or suspension of the salt (16) is treated at low temperature (25° to −30°) with a dry ethereal solution of chloramine. The reaction is stirred for a period of several minutes to several hours. After filtration, the reaction mixture is washed with aqueous bisulfite and then dried and the solvent removed on a rotary evaporator. The crude product is further purified by usual methods such as crystallization or chromatography.

Ortho-heterocyclic-nitrophenyl compounds 10 are known in the art. For a suitable reference, see Elderfield "Heterocyclic Compounds", Vol. 5, Chapters 4, 5 and 8, 1957, J. Wiley and Sons, Inc., New York and R. Lakham and B. Ternai, *Advances in Heterocyclic Chemistry*, 17, 99–212 (1975).

Nitro compounds of Formula (10a) in which Q is

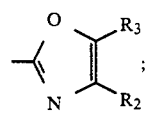

and $R_2$ and $R_3$ are H are prepared by the procedures shown in Equations 11 and 12.

Equation 11

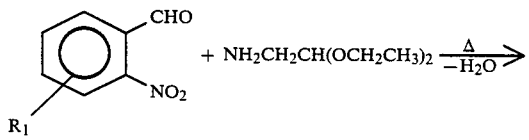

Equation 12

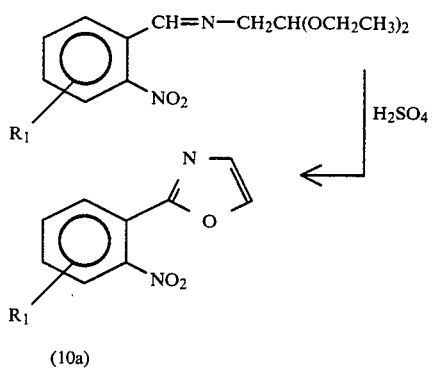

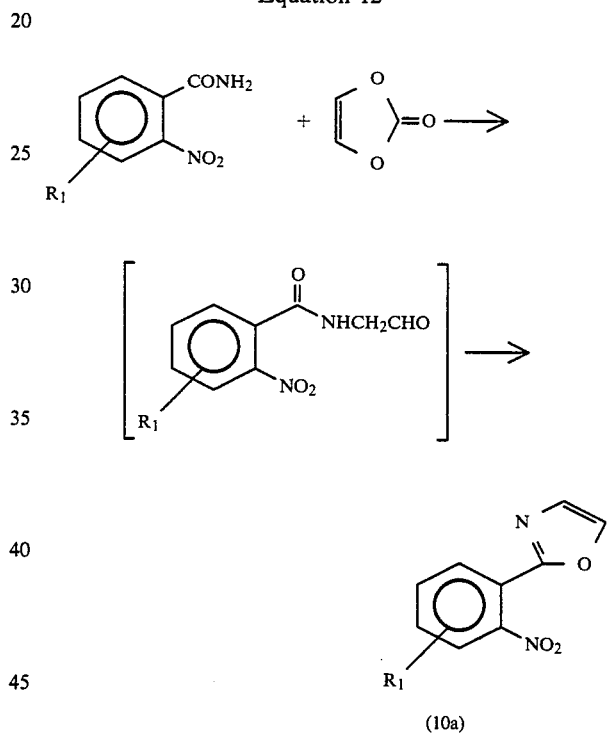

Details of the procedures of Equations 11 and 12 can be found in W. E. Cass, *J. Am. Chem. Soc.*, 64, 785 (1942).

Compounds of Formula (10b) in which Q is

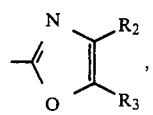

and $R_2$ and $R_3$ are H, $CH_3$ or $CH_3CH_2$ and both $R_2$ and $R_3$ are not simultaneously H, are prepared by the Robinson-Gabriel synthesis of oxazoles from the corresponding acylaminoketones as described in Equation 13. See Elderfield, "Heterocyclic Compounds", Vol. 5, Chapter 5, 1957, J. Wiley & Sons, New York and references therein.

Equation 13

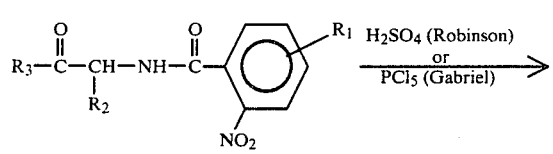

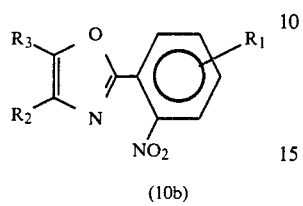

(10b)

Compounds of Formula (10c) in which Q is

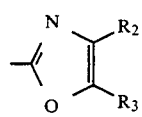

and $R_3$ is $CH_3O$ or $CH_3CH_2O$ and $R_2$ is H, $CH_3$ or $CH_3CH_2$ are prepared as shown in Equation 14. For further details, see Elderfield, location cited above.

Equation 14

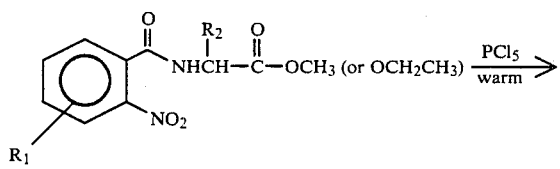

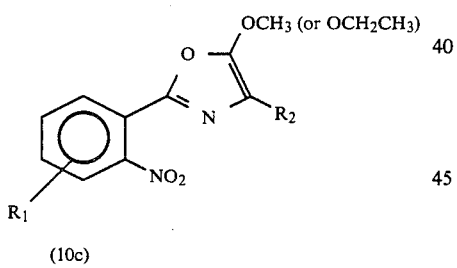

(10c)

Compounds of Formula (10d) in which Q is

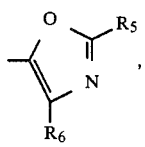

$R_5$ is H and $R_6$ is $CH_3$ or $CH_3CH_2$ are prepared as shown in Equation 15.

Equation 15

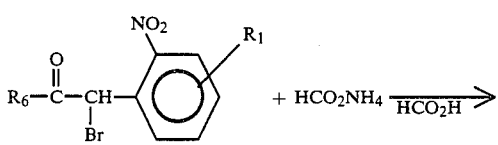

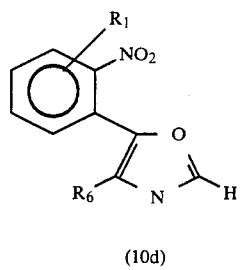

(10d)

Compounds of Formula (10e) in which Q is

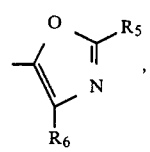

$R_5$ is $CH_3$ or $CH_3CH_2$ and $R_6$ is $CH_3$ or $CH_3CH_2$ are prepared as shown in Equation 16.

Equation 16

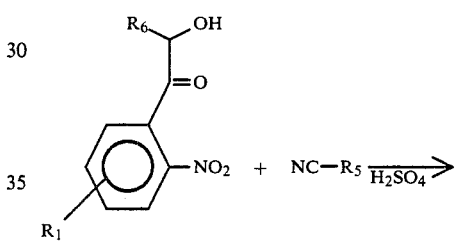

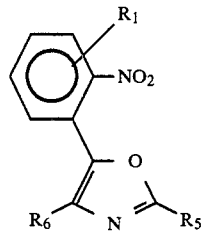

(10e)

For details of the procedure of Equations 15 and 16, see the cited reference on page 22, line 11.

Compounds of Formula (10f) in which Q is

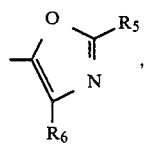

$R_5$ is Cl or Br and $R_6$ is H, $CH_3$ or $CH_3CH_2$ are prepared from the corresponding oxazolone (17) and $POCl_3$ or $POBr_3$ as shown in Equation 17. For details of this procedure, see I. J. Turche, M. J. S. Dewan, *Chem. Rev.*, 75, 391 (1975) page 411 and related references therein.

Equation 17

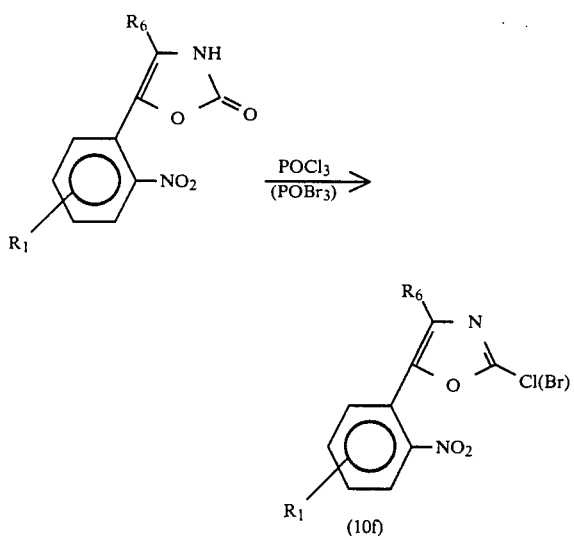

Compounds of Formula (10g) where $R_6$ is H, $CH_3$ or $CH_3CH_2$ and $R_5$ is $CH_3O$, $CH_3CH_2O$ or $CH_3S$ are prepared from (10f) by displacement with the appropriate nucleophile as shown in Equation 18.

Equation 18

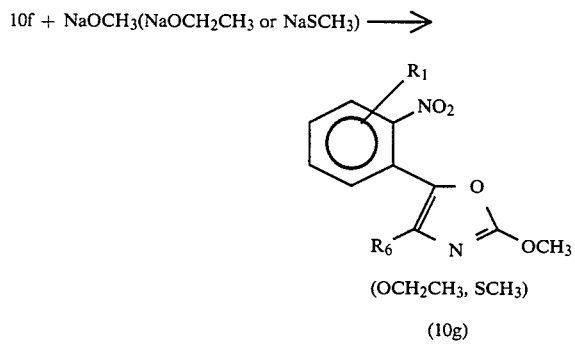

For details of this reaction see the cited reference on page 25, section IIo, page 402 and references cited therein.

The oxazoles in which Q is

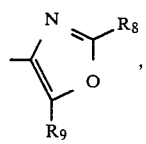

are prepared by analogous procedures to those described in Equations 15, 16, 17 and 18. Substituent limitations are the same.

Compounds of Formula (10h) in which Q is

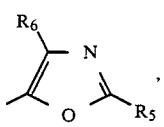

and $R_5$ and $R_6$ are both H are best prepared by the procedures of Equations 19 or 20.

Equation 19

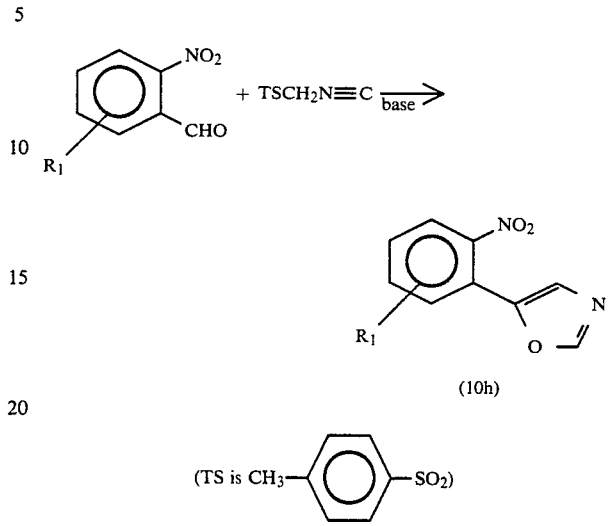

For details of this procedure, see A. M. Van Leusen, B. E. Hoogenboom and H. Sederius, *Tet. Let.* 2369 (1972).

Equation 20

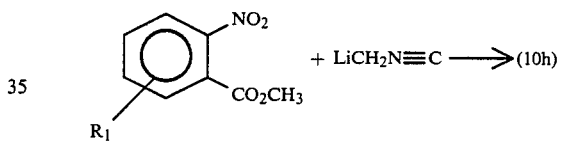

For details of this procedure, see Y. Koyama, K. Yokose and L. Dolby, *Agric. Biol. Chem.*, 45, 1285 (1981).

Alternatively, sulfonamide of Formula Ia where Q is

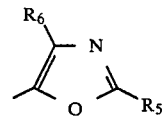

and $R_5$ and $R_6$ are both H can be prepared by the procedure of Equation 20a.

Equation 20a

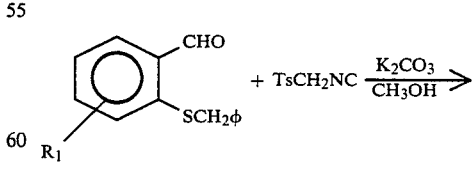

-continued

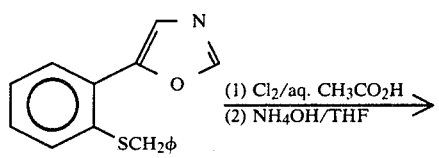

Compounds of Formula (10i) in which Q is

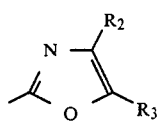

$R_3$ is Cl or Br and $R_2$ is H, $CH_3$, $CH_3CH_2$, $OCH_3$ or $OCH_2CH_3$ are prepared by the procedure of Equation 21.

Equation 21

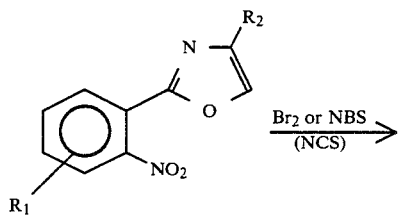

Details and references can be found in I. J. Turchi and M. J. S. Dewar, *Chem. Rev.*, 75, 409 (1975).

Compounds of Formula 10i in which Br or Cl has been replaced by $CH_3O$, $CH_3CH_2O$ or $CH_3S$ are prepared by a displacement reaction with the corresponding nucleophile, using procedures known to those skilled in the art.

Thiazoles

Compounds of Formula (10j) in which Q is

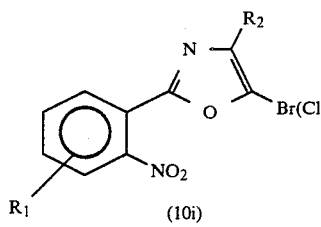

and $R_8$ is H, $CH_3$ or $CH_3CH_2$ and $R_9$ is H, $CH_3$ or $CH_3CH_2$ are prepared by the procedure of Equation 22.

Equation 22

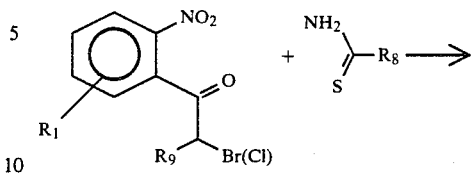

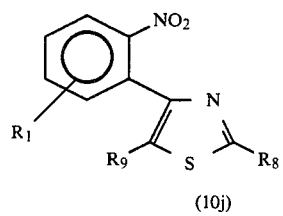

Similarly, compounds of Formula (10k) in which Q is

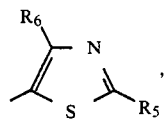

$R_6$ is H, $CH_3$, $CH_3CH_2$ and $R_5$ is H, $CH_3$ or $CH_3CH_2$ are prepared by the procedure of Equation 23.

Equation 23

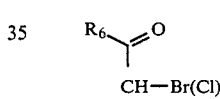

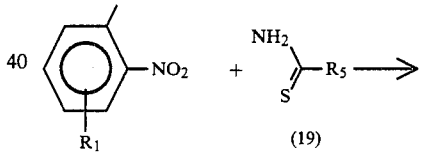

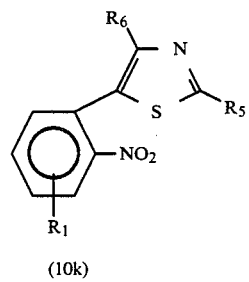

In like fashion to the above, compounds of formula (10l) in which Q is

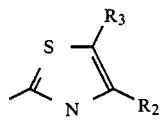

and $R_2$ is $CH_3$ or $CH_3CH_2$, and $R_3$ is H, $CH_3$ or $CH_3CH_2$ are prepared by the procedure of Equation 24.

Equation 24

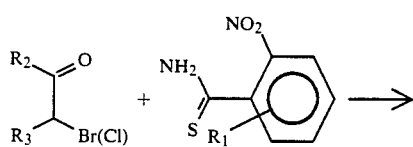

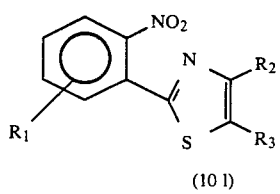

(10 l)

Routes to compounds of Formulas (10m), (10n) and (10p) are available by reaction of the corresponding acylaminocarbonyl compounds with $P_2S_5$ (Gabriel Synthesis) as shown in Equations 25, 26 and 27 respectively.

Equation 25

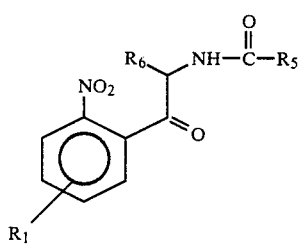

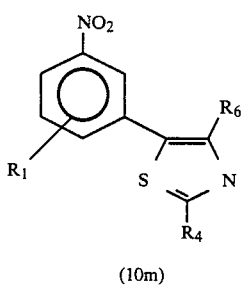

(10m)

where $R_5$ is H, $CH_3$, $CH_3CH_2$, $CH_3O$ or $CH_3CH_2O$;
$R_6$ is $CH_3$, $CH_3CH_2$.

Equation 26

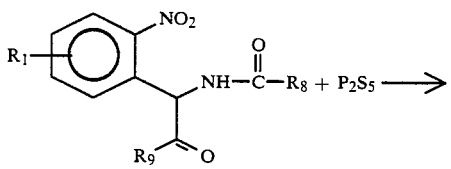

-continued

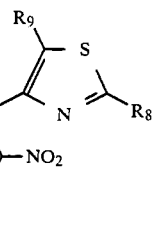

(10n)

where $R_8$ is H, $CH_3$, $CH_3CH_2$, $CH_3O$ or $CH_3CH_2O$;
$R_9$ is $CH_3$ or $CH_3CH_2$.

Equation 27

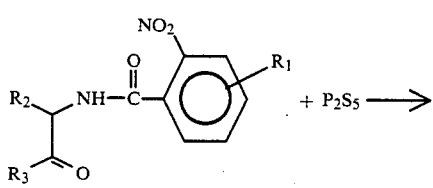

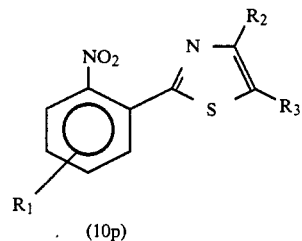

(10p)

where $R_2$ is H, $CH_3$ or Et;
$R_3$ is $CH_3$, $CH_3CH_2$, $CH_3O$ or $CH_3CH_2O$.

For additional details on the procedures of Equations 22–27 see:

(1) J. V. Metzger (ed.), *Chem. Heterocyclic Compounds*, 34, parts (1–3) (1978–1979).

(2) J. M. Sprague and A. H. Land, "Heterocyclic Compounds", (R. C. Elderfield, ed.) V, 484–722. Wiley, N.Y.

Compounds of Formula (10q) in which Q is

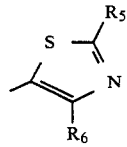

and $R_6$ is H, $CH_3$ or $CH_3CH_2$, and $R_5$ is Cl or Br are prepared via the Sandmeyer reaction on the corresponding amino derivative as shown in Equation 28.

Equation 28

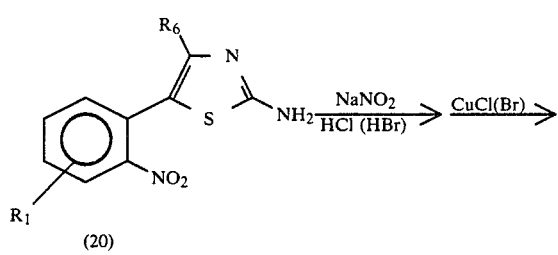

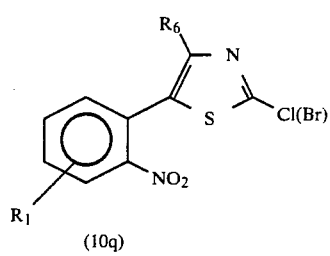

The amino derivatives (20) are prepared by substitution of the thioamide (19) with thiourea (Equation 23). Treatment of (10q) with NaOCH$_3$, NaOCH$_2$CH$_3$ or NaSCH$_3$ by procedures known to one skilled in the art yields the products in which R$_5$ is OCH$_3$, OCH$_2$CH$_3$ or SCH$_3$ in Formula (10q).

In like fashion to the above, compounds of Formula (10s) in which Q is

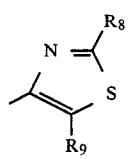

R$_9$ is H, CH$_3$ or CH$_3$CH$_2$ and R$_8$ is Cl, Br, OCH$_3$, OCH$_2$CH$_3$ or SCH$_3$ can be prepared.

Compounds of Formula (10t) in which Q in (10) is

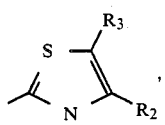

and R$_2$ is H, CH$_3$ or CH$_3$CH$_2$ and R$_3$ is Cl or Br are prepared by the procedure of Equation 29.

Equation 29

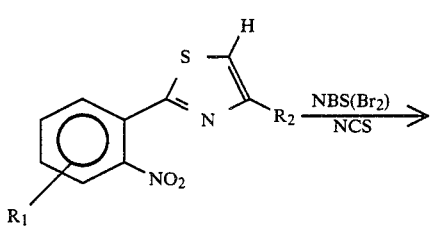

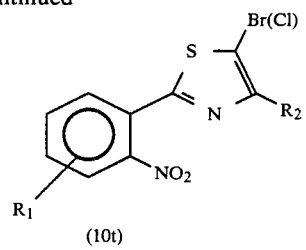

(10t)

Compounds (10t) are in turn used to prepare the corresponding analogs in which Br is replaced by OCH$_3$, OCH$_2$CH$_3$ or SCH$_3$ via displacement.

While OCH$_3$, OCH$_2$CH$_3$ and SCH$_3$ are best introduced at the nitro stage, Cl or Br are best introduced at the sulfonamide stage in order to avoid possible loss of halogen during reduction.

Imidazoles

Compounds of Formula (10u) in which Q in (10) is

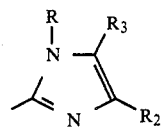

and R is H or C$_1$–C$_4$ alkyl, R$_2$ is H, CH$_3$ or CH$_3$CH$_2$ and R$_3$ is H, CH$_3$ or CH$_3$CH$_2$ are prepared by the procedure of Equation 30.

Equation 30

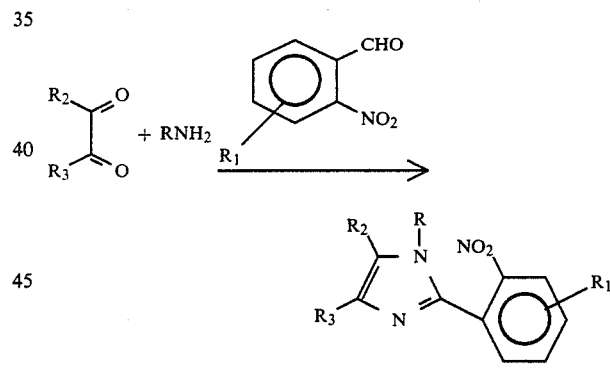

(10u)

Additionally, compound (10u) may be prepared from the corresponding imidazoline (10v) by dehydrogenation with a suitable catalyst (Equation 31).

Equation 31

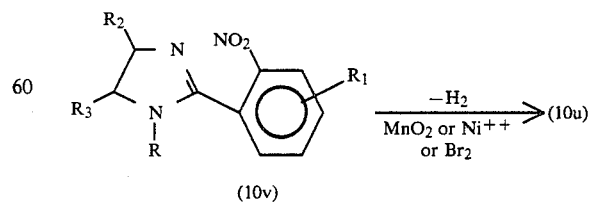

For compounds in which R$_3$ is OCH$_3$, OCH$_2$CH$_3$ or SCH$_3$ in the final product, these substituents are best introduced into the nitro compound (10u) and are prepared by the displacement of compounds in which $R_3$ is Cl or Br in (10u); halogen is introduced by treatment of the compounds of Formula (10u) ($R_3$ is H) with NBS or NCS. To avoid loss of halogen during reduction, halogen is best introduced into the final product at the sulfonamide stage (Equation 32).

Equation 32

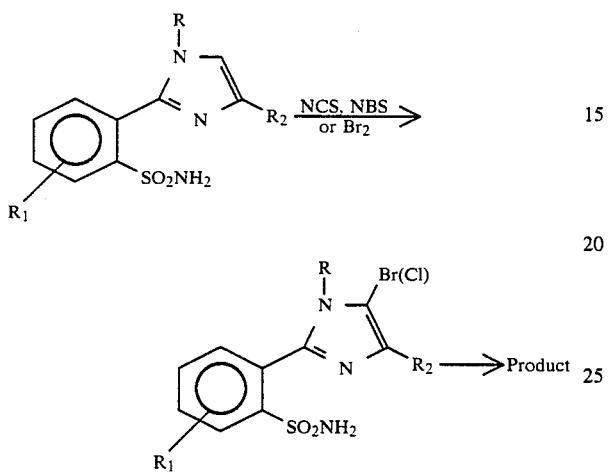

Compounds of Formula (10w) in which Q is

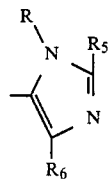

in (10), $R_5$ is H or $CH_3S$ and $R_6$ is H, $CH_3$ or $CH_3CH_2$ are prepared by treatment of the corresponding α-aminoketone with the appropriate isothiocyanate $R_5NCS$ as shown in Equation 33. Similarly prepared are compounds (10x) in which $R_8$ is H or $SCH_3$ and $R_9$ is H, $CH_3$ or $CH_3CH_2$.

Equation 33

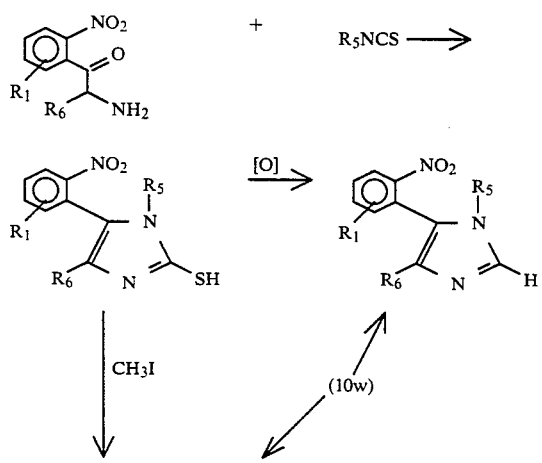

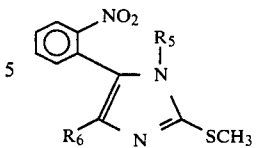

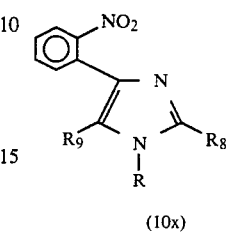

(10x)

Contacting the appropriate α-haloketone with an amidine provides compounds of Formula 10 in which Q is

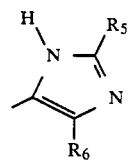

and $R_5$ is H, $CH_3$ or $CH_3CH_2$ as shown in Equation 33-A.

Equation 33-A

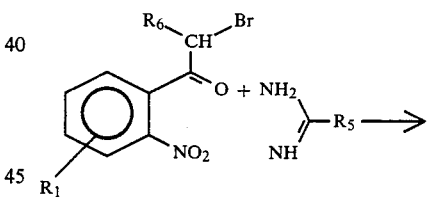

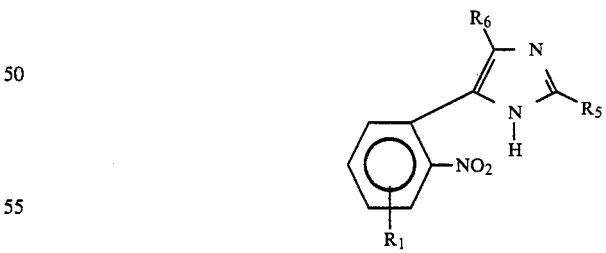

Alkylation of this product with a $C_1$–$C_4$ alkyl iodide using procedures known to those skilled in the art leads to products in which $R_5$ is H, $CH_3$ or $CH_3CH_2$ and R is $C_1$–$C_4$ alkyl.

Also produced in the alkylation are compounds in which R is $C_1$–$C_4$ alkyl and $R_8$ is H, $CH_3$ or $CH_3CH_2$ and $R_9$ is H, $CH_3$ or $CH_3CH_2$ as shown in Equation 33-B.

Equation 33-B

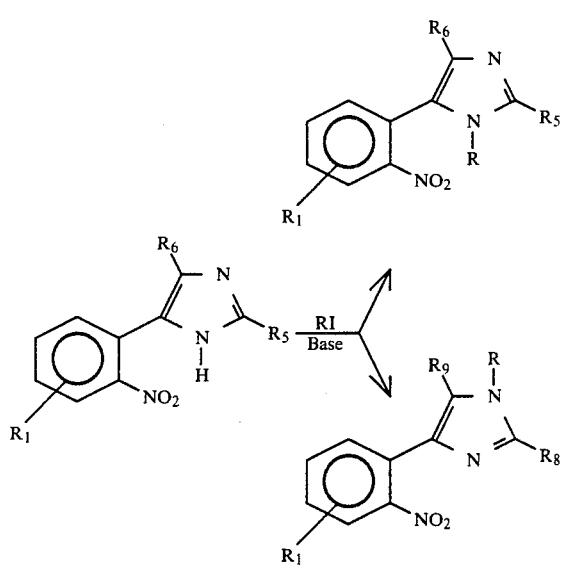

OXAZOLINES, THIAZOLINES AND IMIDAZOLINES

The intermediate oxazolines, thiazolines and imidazolines (14), are required for use in preparing compounds of Formula I in which Q is

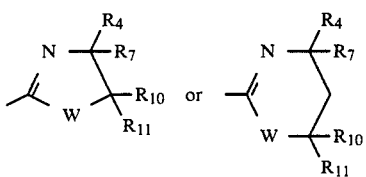

For methods see:

"Heterocyclic Compounds", V, R. C. Elderfield, Editor, John Wiley & Sons, Inc., New York, 1957.

R. J. Fern and J. C. Riebsomer, *Chem. Rev.*, 54, 543–613 (1954).

R. H. Wiley and L. L. Bennett, Jr., *Chem. Rev.*, 44, 447–476 (1944).

Compounds of Formula (10y) in which Q is

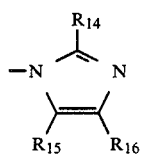

are best prepared by displacement of halogen from the corresponding halo aromatic nitro compound with the imidazole salt as shown in Equation 34.

Equation 34

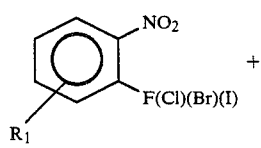
+
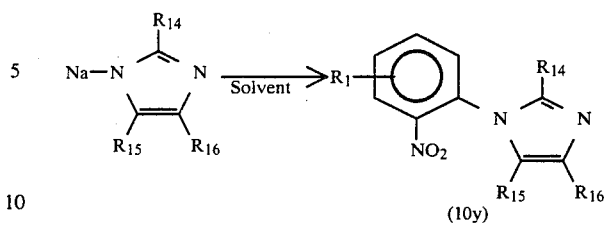

The reaction is conducted in the presence of an appropriate solvent such as dimethylformamide, N-methylpyrrolidone or THF at temperatures from ambient to reflux and for a period of one to twenty-four hours. The procedure is especially useful when $R_{14}$ is H, $CH_3$ or $CH_3CH_2$. When $R_{14}$ is $CH_3S$, $CH_3O$ or $CH_3CH_2O$ in (10y), these substituents are best introduced by displacement of the corresponding iodo, bromo or chloro derivatives of 10y.

For the preparation of 2-haloimidazoles see:

"Heterocyclic Compounds" V, R. C. Elderfield, Editor, John Wiley & Sons, New York, 1957.

K. Hofmann, "The Chemistry of Heterocyclic Compounds," (A. Weissberger, ed.), Vol. 6, pp. 1–420. Wiley (Interscience), New York, 1953.

The following examples serve to more fully illustrate the preparation of compounds of this invention. All temperatures are in degrees centigrade and all parts are by weight unless otherwise indicated.

EXAMPLE 1

Preparation of 2-(2-oxazolyl)benzenamine

To 19.0 g of 2-(2-nitrophenyl)oxazole, (prepared by the procedure of W. E. Cass, *J. Am. Chem. Soc.*, 64, 785 [1942]) 3.0 g of Raney-Nickel catalyst (purchased from Aldrich Chemical Company, Milwaukee, Wis. 53201) and 200 ml ethanol were combined and reduced at ambient temperature and at a $H_2$ pressure of 5–50 psi on a Paar Hydrogenator until the hydrogen uptake ceased. The catalyst was filtered through celite under a blanket of nitrogen. The solvent was removed on a rotary evaporator. 17.4 g of crude product with m.p. 31°–32° was obtained and used in the next step.

EXAMPLE 2

Preparation of 2-(2-oxazolyl)benzenesulfonamide

Diazotization

To 100 ml $H_2O$ and 180 ml of concentrated HCl was added 40.0 g of 2-(2-oxazolyl)benzenamine. The mixture was cooled to 0°–5°. To this mixture was added dropwise a solution of 18.6 g $NaNO_2$ in 30 ml of water, keeping the temperature in the range of 0°–5° during the addition. The reaction mixture was stirred for 15 minutes after the nitrite addition was complete.

Coupling (Sulfonyl Chloride Formation)

A second flask was charged with 100 ml glacial acetic acid, 100 ml concentrated HCl and 4.3 g $CuCl_2$. The mixture was cooled to 0°–10° C.

The diazonium salt was added dropwise to the coupling mixture during a period of 15 minutes while maintaining the temperature between 0°–10° C. The progress of the reaction was monitored by nitrogen evolution via a bubbler attached to the reaction vessel. When nitrogen evolution ceased (approximately 2 hours reaction time), the reaction mixture was poured into 1500 ml ice-water. The crude solid sulfonyl chloride was filtered and converted directly to the sulfonamide in the next step. A small dried sample had a m.p. of 88°–89° C.

Amination (Sulfonamide Formation)

The crude solid product from the previous step was added to a solution of 400 ml tetrahydrofuran containing excess aqueous ammonia and cooled to 10°–15°. The reaction mixture was stirred for 30 minutes. 300–400 ml of water was added to the reaction mixture, which was then extracted several times with $CH_2Cl_2$. The $CH_2Cl_2$ extracts were combined and back extracted with water, then dried with anhydrous $MgSO_4$. The solution of the product was filtered and the solvent removed on a rotary evaporator yielding 36.4 g of crude sulfonamide with m.p. 139°–140°.

EXAMPLE 3

Preparation of N-[(4-methoxy-6-methylpyrimidin-2-yl)-aminocarbonyl]-2-(oxazol-2-yl)benzenesulfonamide Under $N_2$, 5.5 ml of $2M(CH_3)_3Al$ in toluene (purchased from Aldrich Chemical Co., Milwaukee, Wisc.) was added to 2.2 g (0.01 m) of 2-(2-oxazolyl)-benzenesulfonamide dissolved in 80 ml dry $CH_2Cl_2$. The reaction was stirred for 15 minutes after the addition. 2.1 g of solid 4-methoxy-6-methylpyrimidin-2-yl)carbamic acid, methyl ester, (prepared by procedures described previously) was added. The reaction was stirred at ambient temperature for one hour and then refluxed for approximately 16 hours. After cooling to 10° C., 50 ml of water was added cautiously, dropwise, followed by enough glacial HOAc to lower the pH of the reaction mixture to 3.0. The crude reaction mixture was extracted several times with $CH_2Cl_2$. The extracts were dried with anhydrous $Na_2SO_4$, filtered, and the solvent stripped on a rotary evaporator. The crude product was triturated with n-butyl chloride-ethyl acetate 1:1. The resulting solid was filtered yielding 1.6 g product with m.p. 208°–209°(d).

EXAMPLE 4

Preparation of 1-Methyl-2-(2-nitrophenyl)-1H-imidazole

Under $N_2$, 9.5 g of 2-(2-nitrophenyl)-1H-imidazole in a solution of 100 ml dimethylformamide and 25 ml of anhydrous tetrahydrofuran cooled to 0°–5° C., was treated with 2.3 g of a 50% mineral oil dispersion of NaH. After the $N_2$ evolution ceased, 8.5 g of $CH_3I$ was added dropwise over a period of 15 minutes maintaining the temperature at 0°–5°. The reaction mixture was allowed to warm to ambient temperature and then stirred for two hours. The reaction mixture was then poured into water. The aqueous suspension of the product was extracted several times with $CH_2Cl_2$. The extracts were combined and dried with anhydrous $Na_2SO_4$. The solvent was removed on a rotary evaporator. The last traces of dimethylformamide were removed under high vacuum; a waxy solid remained. The crude product was crystallized from $CH_3CN$. Two crops totaling 3.6 g were obtained. The m.p. was 89°–90°.

EXAMPLE 5

Preparation of 2-(1-methyl-1H-imidazol-2-yl)benzenamine 28.0 g Nitro compound from the preceding step was added to 120 ml of concentrated HCl and cooled to 0°–10° C. A solution of 96.6 g of $SnCl_2.2H_2O$ in 120 ml concentrated HCl (cooled to 0°–10° C.) was added to the nitro compound. The reaction mixture was warmed to 50° C. on a steam bath to complete the reduction.

The reaction mixture was poured into ice-water and the pH raised to 10–12 with 50% NaOH solution. The precipitated product was filtered and taken up in $CH_2Cl_2$. The organic solution of the crude product was dried with anhydrous $Na_2SO_4$. The solvent was removed on a rotary evaporator yielding 16.9 g tan product with m.p. 152°–153°.

EXAMPLE 6

Preparation of 2-(1-methyl-1H-imidazol-2-yl)benzenesulfonamide

Diazotization 16.0 g of Amino compound from the preceding step was added to 100 ml of concentrated HCl and cooled to 0°–5°. A solution of 6.7 g $NaNO_2$ in 15 ml of water was added dropwise maintaining the temperature at 0°–5°. The reaction mixture was stirred 10 minutes after the addition was completed.

Coupling

Into a vessel cooled to 0°–5° C. were charged 50.0 ml HCl, 0.16 g $CuCl_2$ and 21.5 ml $SO_2$. The cooled diazonium salt from the preceding step was added dropwise over a period of 10–15 minutes keeping the temperature between 0°–5° C. The reaction was stirred for 1 hour at 0°–5° C. A yellow precipitate formed which was filtered. A small sample of this product was crystallized from $CH_3CN$ and had a m.p. of 215°–218° C. The spectral data and color are more consistent with the tricyclic salt

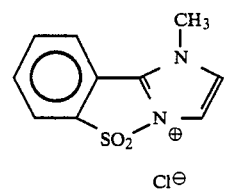

(1H-imidazo[1,2-β][1,2]benzisothiazol-1-ium, 1-methyl-5,5-dioxide chloride) rather than the sulfonyl chloride

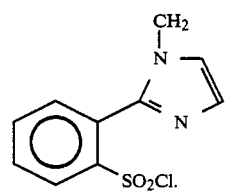

The salt was then aminated as described below.

Amination

The crude yellow solid from the preceding step was dissolved in water and enough concentrated aqueous $NH_3$ was added to raise the pH to 9.0. The reaction mixture was stirred at ambient temperature for about 30 minutes. The reaction mixture was poured into H₂O and then extracted with CH₂Cl₂, dried with anhydrous Na₂SO₄ and the solvent removed on a rotary evaporator. 4.5 g of crude product was obtained. The product was purified by dry column chromatography on silica gel with 1% EtOH/EtOAc. The purified product was washed from the silica with MeOH. The MeOH was removed on a rotary evaporator yielding 3.6 g of product sulfonamide with a m.p. of 158°–163°.

EXAMPLE 7

Preparation of N-[(4,6-dimethoxypyrimidin-2-yl)aminocarbonyl]-2-(1-methyl-1H-imidazol-2-yl)benzenesulfonamide Under N₂, 2.3 ml of a 2M solution of (CH₃)₃Al was added dropwise to a solution of 1.0 g of sulfonamide from the preceding step in 40 ml of CH₂Cl₂. The mixture was stirred at ambient temperature for 15 minutes after which 0.89 g of (4,6-dimethoxypyrimidin-2-yl)carbamic acid, methyl ester was then added. The reaction was stirred at ambient temperature for 15 minutes and then heated to reflux for 16 hours.

The reaction mixture was cooled to 10° and 50 ml of water was added dropwise. The crude reaction mixture was extracted with CH₂Cl₂ several times. The organic extract of the product was dried with anhydrous Na₂SO₄, filtered and the solvent removed on a rotary evaporator. The crude product was triturated with EtOAc and filtered. 0.5 g of product with m.p. 182°–183° was obtained.

EXAMPLE 8

Preparation of 2-(4,5-dihydro-4,4-dimethyloxazole-2-yl)benzenesulfinic acid, lithium salt To 200 ml of dry tetrahydrofuran was added 16.3 g (0.1M) of 2-phenyl-4,4-dimethyl-4,5-dihydrooxazole (prepared by the procedure taught in *J. Org. Chem.*, 28, 2759 [1963]). The solution was cooled to −30° to −40° and 65 ml of 1.6M solution (0.105M) of butyl lithium was added dropwise while maintaining the temperature. After the addition the reaction was allowed to warm to 0°. The reaction was stirred for one hour at 0° and then cooled to −40°. While maintaining the temperature, 4.7 ml of sulfur dioxide was added dropwise. When the last drop of SO₂ was added, the reddish yellow solution of the lithium agent turned lemon yellow. The reaction was stirred for one hour after the addition and allowed to warm to room temperature. The solvent was stripped on a rotary evaporator leaving a solid residue which was triturated with anhydrous ether. The product was filtered and dried in a vacuum oven at 70° C. for 16 hours.

EXAMPLE 9

Preparation of 2-(4,5-dihydro-4,4-dimethyloxazol-2-yl)-benzenesulfonamide 21.0 g of sulfinic acid from the preceding step was dissolved in 150 ml of anhydrous tetrahydrofuran and cooled to −50°. To this mixture was added a solution containing approximately an equivalent amount of chloramine prepared as follows: (see Coleman and Hauser, *J. Am. Chem. Soc.*, 50, 1193 (1928). To 12.0 gms of aqueous NH₃ and 300 ml of ether cooled to 0°–5° C. was added 286 g of aqueous NaOCl (5.25%) also cooled to 0°–5° C. The mixture was stirred for 15 minutes. The ether layer was separated, the aqueous phase was extracted with 100 ml of ether cooled to 0°. The ether extracts were cooled to −30° and dried with anhydrous CaCl₂. The resulting cold ethereal chloramine solution was added to the sulfinic acid maintaining the temperature at −30° to −50°. The reaction mixture was allowed to warm to 0° to −10° C. and stirred for 30 minutes. The reaction mixture was then allowed to warm to ambient temperature over a period of one hour. The reaction mixture was extracted once with an aqueous NaHSO₃ solution and then dried and filtered. The ether was stripped on a rotary evaporator to yield an oil. Trituration with CH₂Cl₂ yielded 1.1 g of product with m.p. 142°–146°. Dry column chromatography of the filtrate on silica gel with ethyl acetate yielded an additional 1.2 g of product with m.p. 138°–142°.

EXAMPLE 10

2-(4,5-dihydro-4,4-dimethyloxazol-2-yl)-N-[(4,6-dichloro-1,3,5-triazin-2-yl)aminocarbonyl]benzenesulfonamide To 1.1 g of sulfonamide from the preceding step dissolved in 15 ml of anhydrous tetrahydrofuran under N₂ at ambient temperature was added a solution of 0.78 g of 4,6-dichloro-1,3,5-triazine isocyanate dissolved in 5 ml of anhydrous tetrahydrofuran. The reaction mixture was refluxed for 30 minutes. After cooling to ambient temperature, the solvent was removed on a rotary evaporator. The crude product was triturated with hexane and filtered yielding 1.7 g which was used in the following step without further purification.

EXAMPLE 11

Preparation of 2-(4,5-dihydro-4,4-dimethyloxazol-2-yl)-N-[(4,6-dimethoxy-1,3,5-triazin-2-yl)aminocarbonyl]benzenesulfonamide To 5 ml of CH₃OH was added 0.4 g of urea from the preceding step. Solid NaOCH₃ (0.157 g) was added and the reaction mixture refluxed for 30 minutes. The reaction mixture was poured into 50 ml H₂O. The aqueous solution was extracted with CH₂Cl₂ and the organic extract discarded. The pH was lowered to 3.0 with HOAc. The aqueous solution was then extracted with CH₂Cl₂ and the extracts were combined, dried with anhydrous Na₂SO₄, filtered and the solvent was removed on a rotary evaporator yielding 300 mg of crude product, i.r. (nujol) 5.82μ (C=O).

EXAMPLE 12

Preparation of 5-[(2-phenylmethylthio)phenyl]oxazole

A mixture of 22.8 g 2-(phenylmethylthio)benzaldehyde (prepared by the procedure of G. W. Stacy, et al., *J. Org. Chem.*, 35, 3495 (1970)), 19.5 g of p-toluenesulfonylmethylisocyanide, 13.8 g of anhydrous potassium carbonate and 150 ml methanol were heated at reflux for 3.75 hours. The reaction solution was cooled and the solvent evaporated under reduced pressure. The resulting oily solid was partitioned between water and ether. The organic phase was dried over anhydrous magnesium sulfate, filtered, and the solvent evaporated under reduced pressure. Distillation of the crude oil gave 16.4 g of the title compound as a viscous yellow-orange oil, bp 180°–194° (0.7–1.0 mm); NMR (CDCl₃) δ 4.05 (s, 2H, CH$_2$), 7.2-7.6 (m, 9H, aromatic), 7.8 (s, 1H, CH) and 7.95 (s, 1H, CH).

EXAMPLE 13

Preparation of 2-(oxazol-5-yl)benzenesulfonamide

A solution of 16.0 g of 5-[(2-phenylmethylthio)-phenyl]oxazole in a mixture of 100 ml of acetic acid and 10 ml of water was cooled to 5° and 9.1 ml of chlorine was added portionwise while maintaining the temperature below 15°. When addition of chlorine was complete, the yellow-brown solution was stirred 15 minutes at 5°-10° then poured into 600 ml of ice water. The aqueous mixture was extracted with ether. The organic solution was washed with water (3×250 ml) followed by brine (50 ml), then dried over anhydrous magnesium sulfate, filtered and the solvent removed under reduced pressure. The crude reaction product was dissolved in 150 ml of tetrahydrofuran and cooled to 0°-5°. Ammonium hydroxide (8.0 ml) was added dropwise. The red-orange suspension was stirred 20 minutes at 0°-5° then allowed to warm to ambient temperature and stirred until TLC (Hexane/ethyl acetate-1:1) showed no sulfenyl chloride remained. The solvent was removed under reduced pressure and the resulting oily solid triturated with 250 ml of cold water. The resulting oily solid was collected and washed sequentially with water, butyl chloride/hexane (1:1), isopropyl alcohol and butyl chloride giving 7.1 g of the title compound as a slightly yellow solid, m.p. 157°-163°; ir (mull) 3420 and 3210 cm$^{-1}$ (NH$_2$).

Using analogous procedures to those described in Examples 1-13, the following compounds may be prepared.

In Tables 1-16, the headings refer to the following structure

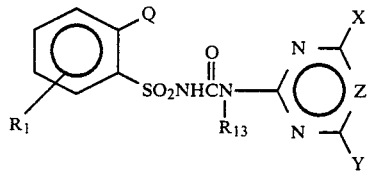

TABLE 1

[In Formula I] Q is 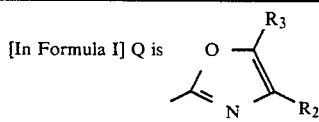

| R$_1$ | R$_{13}$ | R$_2$ | R$_3$ | X | Y | Z | m.p.(°C.) |
|---|---|---|---|---|---|---|---|
| 5-F | H | H | H | CH$_3$ | CH$_3$ | N | |
| 6-Cl | H | H | H | CH$_3$ | OCH$_3$ | N | |
| 4-Br | H | H | H | OCH$_3$ | OCH$_3$ | N | |
| 3-CH$_3$ | H | H | H | CH$_3$ | CH$_3$ | CH | |
| 5-OCH$_3$ | H | H | H | CH$_3$ | OCH$_3$ | CH | |
| 5-CF$_3$ | H | H | H | OCH$_3$ | OCH$_3$ | CH | |
| H | CH$_3$ | H | H | CH$_3$ | CH$_3$ | N | |
| H | CH$_3$ | H | H | CH$_3$ | OCH$_3$ | N | |
| H | CH$_3$ | H | H | OCH$_3$ | OCH$_3$ | N | |
| H | CH$_3$ | H | H | CH$_3$ | CH$_3$ | CH | |
| H | CH$_3$ | H | H | OCH$_3$ | CH$_3$ | CH | |
| H | CH$_3$ | H | H | OCH$_3$ | OCH$_3$ | CH | |
| H | H | H | H | Cl | OCH$_3$ | CH | |
| H | H | H | H | Cl | NH$_2$ | CH | |
| H | H | H | H | Cl | NHCH$_3$ | CH | |
| H | H | H | H | Cl | N(CH$_3$)$_2$ | CH | |
| H | H | H | H | CH$_3$ | CH$_2$CH$_3$ | CH | |
| H | H | H | H | OCH$_3$ | CH$_2$OCH$_3$ | N | |
| H | H | H | H | CH$_3$ | OCH$_2$CH$_3$ | N | |
| H | H | H | H | OCH$_3$ | OCH$_2$CH$_3$ | CH | |
| H | H | H | H | CH$_3$ | CH(OCH$_3$)$_2$ | CH | |
| H | H | H | H | CH$_3$ | CH$_3$ | N | 207-209° |
| H | H | H | H | OCH$_3$ | CH$_3$ | N | 199-201° |
| H | H | H | H | OCH$_3$ | OCH$_3$ | N | 191-192° |
| H | H | H | H | CH$_3$ | CH$_3$ | CH | 213-214° |
| H | H | H | H | OCH$_3$ | CH$_3$ | CH | 208-209° |
| H | H | H | H | OCH$_3$ | OCH$_3$ | CH | 197-200° |
| H | H | CH$_3$ | H | CH$_3$ | CH$_3$ | N | |
| H | H | CH$_3$CH$_2$ | H | OCH$_3$ | CH$_3$ | N | |
| H | H | H | CH$_3$ | OCH$_3$ | OCH$_3$ | N | |
| H | H | H | CH$_3$CH$_2$ | CH$_3$ | CH$_3$ | CH | |
| H | H | H | OCH$_3$ | OCH$_3$ | CH$_3$ | CH | |
| H | H | H | OCH$_2$CH$_3$ | OCH$_3$ | OCH$_3$ | CH | |
| H | H | H | SCH$_3$ | CH$_3$ | OCH$_3$ | N | |
| H | H | H | Cl | OCH$_3$ | OCH$_3$ | CH | |
| H | H | H | Br | OCH$_3$ | CH$_3$ | CH | |
| H | H | H | H | OCH$_3$ | SCH$_3$ | N | |
| H | H | H | H | CH$_3$ | CF$_3$ | CH | |
| H | H | H | H | CH$_3$ | OCH$_2$CF$_3$ | CH | |
| H | H | H | H | CH$_3$ | OCF$_2$CF$_3$ | N | |
| H | H | H | H | CH$_3$ | OCH$_2$CH$_2$OCH$_3$ | N | |
| H | H | H | H | CH$_3$ | CH$_2$OCH$_3$ | CH | |

TABLE 2

[In Formula I] Q is  S–C(R₃)=C(R₂)–N=C<

| R₁ | R₁₃ | R₂ | R₃ | X | Y | Z |
|---|---|---|---|---|---|---|
| 5-F | H | H | H | CH₃ | CH₃ | N |
| 6-Cl | H | H | H | CH₃ | OCH₃ | N |
| 4-Br | H | H | H | OCH₃ | OCH₃ | N |
| 3-CH₃ | H | H | H | CH₃ | CH₃ | CH |
| 5-OCH₃ | H | H | H | CH₃ | OCH₃ | CH |
| 5-CF₃ | H | H | H | OCH₃ | OCH₃ | CH |
| H | CH₃ | H | H | CH₃ | CH₃ | N |
| H | CH₃ | H | H | CH₃ | OCH₃ | N |
| H | CH₃ | H | H | OCH₃ | OCH₃ | N |
| H | CH₃ | H | H | CH₃ | CH₃ | CH |
| H | CH₃ | H | H | OCH₃ | CH₃ | CH |
| H | CH₃ | H | H | OCH₃ | OCH₃ | CH |
| H | H | H | H | CH₃ | OCH₃ | CH |
| H | H | H | H | Cl | NH₂ | CH |
| H | H | H | H | Cl | NHCH₃ | CH |
| H | H | H | H | CH₃ | CH₂CH₃ | CH |
| H | H | H | H | OCH₃ | CH₂OCH₃ | N |
| H | H | H | H | CH₃ | OCH₂CH₃ | N |
| H | H | H | H | OCH₃ | OCH₂CH₃ | CH |
| H | H | H | H | CH₃ | CH(OCH₃)₂ | CH |
| H | H | H | H | CH₃ | CH₃ | N |
| H | H | H | H | OCH₃ | CH₃ | N |
| H | H | H | H | OCH₃ | OCH₃ | N |
| H | H | H | H | CH₃ | CH₃ | CH |
| H | H | H | H | OCH₃ | CH₃ | CH |
| H | H | H | H | OCH₃ | OCH₃ | CH |
| H | H | CH₃ | H | CH₃ | CH₃ | N |
| H | H | CH₃CH₂ | H | OCH₃ | CH₃ | N |
| H | H | H | CH₃ | OCH₃ | OCH₃ | N |
| H | H | H | CH₃CH₂ | CH₃ | CH₃ | CH |
| H | H | H | OCH₃ | OCH₃ | CH₃ | CH |
| H | H | H | OCH₂CH₃ | OCH₃ | OCH₃ | CH |
| H | H | H | SCH₃ | CH₃ | OCH₃ | N |
| H | H | H | Cl | OCH₃ | OCH₃ | N |
| H | H | H | Br | OCH₃ | CH₃ | CH |
| H | H | H | H | OCH₃ | SCH₃ | N |
| H | H | H | H | CH₃ | CF₃ | CH |
| H | H | H | H | CH₃ | OCH₂CF₃ | CH |
| H | H | H | H | CH₃ | OCF₂CF₃ | N |
| H | H | H | H | CH₃ | OCH₂CH₂OCH₃ | N |
| H | H | H | H | CH₃ | CH₂OCH₃ | CH |

TABLE 3

[In Formula I] Q is  N(R)–C(R₃)=C(R₂)–N=C<

| R | R₁ | R₁₃ | R₂ | R₃ | X | Y | Z | m.p.(°C.) |
|---|---|---|---|---|---|---|---|---|
| CH₃ | H | H | H | H | CH₃ | CH₃ | N | |
| CH₃CH₂ | H | H | H | H | OCH₃ | CH₃ | N | |
| CH₃CH₂CH₂ | H | H | H | H | OCH₃ | OCH₃ | N | |
| (CH₃)₂CH | H | H | H | H | CH₃ | CH₃ | CH | |
| CH₃CH₂CH₂CH₂ | H | H | H | H | OCH₃ | CH₃ | CH | |
| (CH₃)₂CHCH₂— | H | H | H | H | OCH₃ | OCH₃ | CH | |
| CH₃CHCH₂CH₃ | H | H | H | H | CH₃ | CH₃ | N | |
| (CH₃)₃C | H | H | H | H | CH₃ | CH₃ | N | |
| H | H | H | H | H | OCH₃ | OCH₃ | N | |
| CH₃ | 5-F | H | H | H | CH₃ | CH₃ | N | |
| CH₃ | 6-Cl | H | H | H | CH₃ | OCH₃ | N | |
| CH₃ | 4-Br | H | H | H | OCH₃ | OCH₃ | N | |
| CH₃ | 3-CH₃ | H | H | H | CH₃ | CH₃ | CH | |
| CH₃ | 5-OCH₃ | H | H | H | CH₃ | OCH₃ | CH | |
| CH₃ | 5-CF₃ | H | H | H | OCH₃ | OCH₃ | CH | |
| CH₃ | H | CH₃ | H | H | CH₃ | CH₃ | N | |
| CH₃ | H | CH₃ | H | H | CH₃ | OCH₃ | N | |
| CH₃ | H | CH₃ | H | H | OCH₃ | OCH₃ | N | |
| CH₃ | H | CH₃ | H | H | CH₃ | CH₃ | CH | |
| CH₃ | H | CH₃ | H | H | OCH₃ | CH₃ | CH | |
| CH₃ | H | CH₃ | H | H | OCH₃ | OCH₃ | CH | |

TABLE 3-continued

[In Formula I] Q is 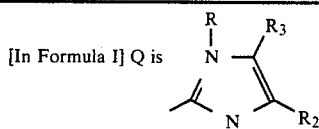

| R | $R_1$ | $R_{13}$ | $R_2$ | $R_3$ | X | Y | Z | m.p.(°C.) |
|---|---|---|---|---|---|---|---|---|
| $CH_3$ | H | H | H | H | Cl | $OCH_3$ | CH | |
| $CH_3$ | H | H | H | H | Cl | $NH_2$ | CH | |
| $CH_3$ | H | H | H | H | Cl | $NHCH_3$ | CH | |
| $CH_3$ | H | H | H | H | Cl | $N(CH_3)_2$ | CH | |
| $CH_3$ | H | H | H | H | $CH_3$ | $CH_2CH_3$ | CH | |
| $CH_3$ | H | H | H | H | $OCH_3$ | $CH_2OCH_3$ | N | |
| $CH_3$ | H | H | H | H | $CH_3$ | $OCH_2CH_3$ | N | |
| $CH_3$ | H | H | H | H | $OCH_3$ | $OCH_2CH_3$ | CH | |
| $CH_3$ | H | H | H | H | $CH_3$ | $CH(OCH_3)_2$ | CH | |
| $CH_3$ | H | H | H | H | $CH_3$ | $CH_3$ | N | |
| $CH_3$ | H | H | H | H | $OCH_3$ | $CH_3$ | N | |
| $CH_3$ | H | H | H | H | $OCH_3$ | $OCH_3$ | N | |
| $CH_3$ | H | H | H | H | $CH_3$ | $CH_3$ | CH | 175–177° |
| $CH_3$ | H | H | H | H | $OCH_3$ | $CH_3$ | CH | 200–205° |
| $CH_3$ | H | H | H | H | $OCH_3$ | $OCH_3$ | CH | 182–183° |
| $CH_3$ | H | H | $CH_3$ | H | $CH_3$ | $CH_3$ | N | |
| $CH_3$ | H | H | $CH_3CH_2$ | H | $OCH_3$ | $CH_3$ | N | |
| $CH_3$ | H | H | H | $CH_3$ | $OCH_3$ | $OCH_3$ | N | |
| $CH_3$ | H | H | H | $CH_3CH_2$ | $CH_3$ | $CH_3$ | CH | |
| $CH_3$ | H | H | H | $OCH_3$ | $OCH_3$ | $CH_3$ | CH | |
| $CH_3$ | H | H | H | $OCH_2CH_3$ | $OCH_3$ | $OCH_3$ | CH | |
| $CH_3$ | H | H | H | $SCH_3$ | $CH_3$ | $OCH_3$ | N | |
| $CH_3$ | H | H | H | Cl | $OCH_3$ | $OCH_3$ | N | |
| $CH_3$ | H | H | H | Br | $OCH_3$ | $CH_3$ | CH | |
| H | H | H | H | H | $OCH_3$ | $SCH_3$ | N | |
| H | H | H | H | H | $CH_3$ | $CF_3$ | CH | |
| H | H | H | H | H | $CH_3$ | $OCH_2CF_3$ | CH | |
| H | H | H | H | H | $CH_3$ | $OCF_2CF_3$ | N | |
| H | H | H | H | H | $CH_3$ | $OCH_2CH_2OCH_3$ | N | |
| H | H | H | H | H | $CH_3$ | $CH_2OCH_3$ | CH | |

TABLE 4

[In Formula I] Q is 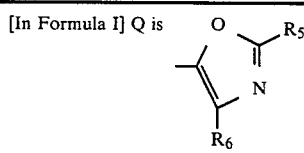

| $R_1$ | $R_{13}$ | $R_6$ | $R_5$ | X | Y | Z |
|---|---|---|---|---|---|---|
| 5-F | H | H | H | $CH_3$ | $CH_3$ | N |
| 6-Cl | H | H | H | $CH_3$ | $OCH_3$ | N |
| 4-Br | H | H | H | $OCH_3$ | $OCH_3$ | N |
| 3-$CH_3$ | H | H | H | $CH_3$ | $CH_3$ | CH |
| 5-$OCH_3$ | H | H | H | $CH_3$ | $OCH_3$ | CH |
| 5-$CF_3$ | H | H | H | $OCH_3$ | $OCH_3$ | CH |
| H | $CH_3$ | H | H | $CH_3$ | $CH_3$ | N |
| H | $CH_3$ | H | H | $CH_3$ | $OCH_3$ | N |
| H | $CH_3$ | H | H | $OCH_3$ | $OCH_3$ | N |
| H | $CH_3$ | H | H | $CH_3$ | $CH_3$ | CH |
| H | $CH_3$ | H | H | $OCH_3$ | $CH_3$ | CH |
| H | $CH_3$ | H | H | $OCH_3$ | $OCH_3$ | CH |
| H | H | H | H | Cl | $OCH_3$ | CH |
| H | H | H | H | Cl | $NH_2$ | CH |
| H | H | H | H | Cl | $NHCH_3$ | CH |
| H | H | H | H | Cl | $N(CH_3)_2$ | CH |
| H | H | H | H | $CH_3$ | $CH_2CH_3$ | CH |
| H | H | H | H | $OCH_3$ | $CH_2OCH_3$ | N |
| H | H | H | H | $CH_3$ | $OCH_2CH_3$ | N |
| H | H | H | H | $OCH_3$ | $OCH_2CH_3$ | CH |
| H | H | H | H | $CH_3$ | $CH(OCH_3)_2$ | CH |
| H | H | H | H | $CH_3$ | $CH_3$ | N |
| H | H | H | H | $OCH_3$ | $CH_3$ | N |
| H | H | H | H | $OCH_3$ | $OCH_3$ | N |
| H | H | H | H | $CH_3$ | $CH_3$ | CH |
| H | H | H | H | $OCH_3$ | $CH_3$ | CH |
| H | H | H | H | $OCH_3$ | $OCH_3$ | CH |
| H | H | $CH_3$ | H | $CH_3$ | $CH_3$ | N |
| H | H | $CH_3CH_2$ | H | $OCH_3$ | $CH_3$ | N |
| H | H | H | $CH_3$ | $OCH_3$ | $OCH_3$ | N |
| H | H | H | $CH_3CH_2$ | $CH_3$ | $CH_3$ | CH |

TABLE 4-continued

[In Formula I] Q is 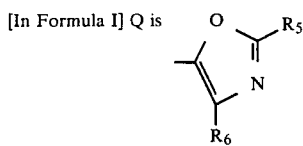

| $R_1$ | $R_{13}$ | $R_6$ | $R_5$ | X | Y | Z |
|---|---|---|---|---|---|---|
| H | H | H | $OCH_3$ | $OCH_3$ | $CH_3$ | CH |
| H | H | H | $OCH_2CH_3$ | $OCH_3$ | $OCH_3$ | CH |
| H | H | H | $SCH_3$ | $CH_3$ | $OCH_3$ | N |
| H | H | H | Cl | $OCH_3$ | $OCH_3$ | N |
| H | H | H | Br | $OCH_3$ | $CH_3$ | CH |
| H | H | H | H | $OCH_3$ | $SCH_3$ | N |
| H | H | H | H | $CH_3$ | $CF_3$ | CH |
| H | H | H | H | $CH_3$ | $OCH_2CF_3$ | CH |
| H | H | H | H | $CH_3$ | $OCF_2CF_3$ | N |
| H | H | H | H | $CH_3$ | $OCH_2CH_2OCH_3$ | N |
| H | H | H | H | $CH_3$ | $CH_2OCH_3$ | CH |

TABLE 5

[In Formula I] Q is 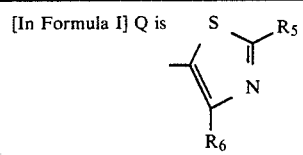

| $R_1$ | $R_{13}$ | $R_6$ | $R_5$ | X | Y | Z |
|---|---|---|---|---|---|---|
| 5-F | H | H | H | $CH_3$ | $CH_3$ | N |
| 6-Cl | H | H | H | $CH_3$ | $OCH_3$ | N |
| 4-Br | H | H | H | $OCH_3$ | $OCH_3$ | N |
| 3-$CH_3$ | H | H | H | $CH_3$ | $CH_3$ | CH |
| 5-$OCH_3$ | H | H | H | $CH_3$ | $OCH_3$ | CH |
| 5-$CF_3$ | H | H | H | $OCH_3$ | $OCH_3$ | CH |
| H | $CH_3$ | H | H | $CH_3$ | $CH_3$ | N |
| H | $CH_3$ | H | H | $CH_3$ | $OCH_3$ | N |
| H | $CH_3$ | H | H | $OCH_3$ | $OCH_3$ | N |
| H | $CH_3$ | H | H | $CH_3$ | $CH_3$ | CH |
| H | $CH_3$ | H | H | $OCH_3$ | $CH_3$ | CH |
| H | $CH_3$ | H | H | $OCH_3$ | $OCH_3$ | CH |
| H | H | H | H | Cl | $OCH_3$ | CH |
| H | H | H | H | Cl | $NH_2$ | CH |
| H | H | H | H | Cl | $NHCH_3$ | CH |
| H | H | H | H | Cl | $N(CH_3)_2$ | CH |
| H | H | H | H | $CH_3$ | $CH_2CH_3$ | CH |
| H | H | H | H | $OCH_3$ | $CH_2OCH_3$ | N |
| H | H | H | H | $CH_3$ | $OCH_2CH_3$ | N |
| H | H | H | H | $OCH_3$ | $OCH_2CH_3$ | CH |
| H | H | H | H | $CH_3$ | $CH(OCH_3)_2$ | CH |
| H | H | H | H | $CH_3$ | $CH_3$ | N |
| H | H | H | H | $OCH_3$ | $CH_3$ | N |
| H | H | H | H | $OCH_3$ | $OCH_3$ | N |
| H | H | H | H | $CH_3$ | $CH_3$ | CH |
| H | H | H | H | $OCH_3$ | $CH_3$ | CH |
| H | H | H | H | $OCH_3$ | $OCH_3$ | CH |
| H | H | $CH_3$ | H | $CH_3$ | $CH_3$ | N |
| H | H | $CH_3CH_2$ | H | $OCH_3$ | $CH_3$ | N |
| H | H | H | $CH_3$ | $OCH_3$ | $OCH_3$ | N |
| H | H | H | $CH_3CH_2$ | $CH_3$ | $CH_3$ | CH |
| H | H | H | $OCH_3$ | $OCH_3$ | $CH_3$ | CH |
| H | H | H | $OCH_2CH_3$ | $OCH_3$ | $OCH_3$ | CH |
| H | H | H | $SCH_3$ | $CH_3$ | $OCH_3$ | N |
| H | H | H | Cl | $OCH_3$ | $OCH_3$ | N |
| H | H | H | Br | $OCH_3$ | $CH_3$ | CH |
| H | H | H | H | $OCH_3$ | $SCH_3$ | N |
| H | H | H | H | $CH_3$ | $CF_3$ | CH |
| H | H | H | H | $CH_3$ | $OCH_2CF_3$ | CH |
| H | H | H | H | $CH_3$ | $OCF_2CF_3$ | N |
| H | H | H | H | $CH_3$ | $OCH_2CH_2OCH_3$ | N |
| H | H | H | H | $CH_3$ | $CH_2OCH_3$ | CH |

TABLE 6

[In Formula I] Q is a pyrrole with substituents R (on N), R$_5$, R$_6$

| R | R$_1$ | R$_{13}$ | R$_6$ | R$_5$ | X | Y | Z |
|---|---|---|---|---|---|---|---|
| CH$_3$ | H | H | H | H | CH$_3$ | CH$_3$ | N |
| CH$_3$CH$_2$ | H | H | H | H | OCH$_3$ | CH$_3$ | N |
| CH$_3$CH$_2$CH$_2$ | H | H | H | H | OCH$_3$ | OCH$_3$ | N |
| (CH$_3$)$_2$CH | H | H | H | H | CH$_3$ | CH$_3$ | CH |
| CH$_3$CH$_2$CH$_2$CH$_2$ | H | H | H | H | OCH$_3$ | CH$_3$ | CH |
| (CH$_3$)$_2$CHCH$_2$— | H | H | H | H | OCH$_3$ | OCH$_3$ | CH |
| CH$_3$CHCH$_2$CH$_3$ | H | H | H | H | CH$_3$ | CH$_3$ | N |
| (CH$_3$)$_3$C | H | H | H | H | OCH$_3$ | CH$_3$ | N |
| H | H | H | H | H | OCH$_3$ | OCH$_3$ | N |
| CH$_3$ | 5-F | H | H | H | CH$_3$ | CH$_3$ | N |
| CH$_3$ | 6-Cl | H | H | H | CH$_3$ | OCH$_3$ | N |
| CH$_3$ | 4-Br | H | H | H | OCH$_3$ | OCH$_3$ | N |
| CH$_3$ | 3-CH$_3$ | H | H | H | CH$_3$ | CH$_3$ | CH |
| CH$_3$ | 5-OCH$_3$ | H | H | H | CH$_3$ | OCH$_3$ | CH |
| CH$_3$ | 5-CF$_3$ | H | H | H | OCH$_3$ | OCH$_3$ | CH |
| CH$_3$ | H | CH$_3$ | H | H | CH$_3$ | CH$_3$ | N |
| CH$_3$ | H | CH$_3$ | H | H | CH$_3$ | OCH$_3$ | N |
| CH$_3$ | H | CH$_3$ | H | H | OCH$_3$ | OCH$_3$ | N |
| CH$_3$ | H | CH$_3$ | H | H | CH$_3$ | CH$_3$ | CH |
| CH$_3$ | H | CH$_3$ | H | H | OCH$_3$ | CH$_3$ | CH |
| CH$_3$ | H | CH$_3$ | H | H | OCH$_3$ | OCH$_3$ | CH |
| CH$_3$ | H | H | H | H | Cl | OCH$_3$ | CH |
| CH$_3$ | H | H | H | H | Cl | NH$_2$ | CH |
| CH$_3$ | H | H | H | H | Cl | NHCH$_3$ | CH |
| CH$_3$ | H | H | H | H | Cl | N(CH$_3$)$_2$ | CH |
| CH$_3$ | H | H | H | H | CH$_3$ | CH$_2$CH$_3$ | CH |
| CH$_3$ | H | H | H | H | OCH$_3$ | CH$_2$OCH$_3$ | N |
| CH$_3$ | H | H | H | H | CH$_3$ | OCH$_2$CH$_3$ | N |
| H | CH$_3$ | H | H | H | OCH$_3$ | OCH$_2$CH$_3$ | CH |
| H | CH$_3$ | H | H | H | CH$_3$ | CH(OCH$_3$)$_2$ | CH |
| H | CH$_3$ | H | H | H | CH$_3$ | CH$_3$ | N |
| H | CH$_3$ | H | H | H | OCH$_3$ | CH$_3$ | N |
| H | CH$_3$ | H | H | H | OCH$_3$ | OCH$_3$ | N |
| H | CH$_3$ | H | H | H | CH$_3$ | CH$_3$ | CH |
| H | CH$_3$ | H | H | H | OCH$_3$ | CH$_3$ | CH |
| H | CH$_3$ | H | H | H | OCH$_3$ | OCH$_3$ | CH |
| H | CH$_3$ | H | CH$_3$ | H | CH$_3$ | CH$_3$ | N |
| H | CH$_3$ | H | CH$_3$CH$_2$ | H | OCH$_3$ | CH$_3$ | N |
| H | CH$_3$ | H | H | CH$_3$ | OCH$_3$ | OCH$_3$ | N |
| H | CH$_3$ | H | H | CH$_3$CH$_2$ | CH$_3$ | CH$_3$ | CH |
| H | CH$_3$ | H | H | OCH$_3$ | OCH$_3$ | CH$_3$ | CH |
| H | CH$_3$ | H | H | OCH$_2$CH$_3$ | OCH$_3$ | OCH$_3$ | CH |
| H | CH$_3$ | H | H | SCH$_3$ | CH$_3$ | OCH$_3$ | N |
| H | CH$_3$ | H | H | Cl | OCH$_3$ | OCH$_3$ | N |
| H | CH$_3$ | H | H | Br | OCH$_3$ | CH$_3$ | CH |
| H | H | H | H | H | OCH$_3$ | SCH$_3$ | N |
| H | H | H | H | H | CH$_3$ | CF$_3$ | CH |
| H | H | H | H | H | CH$_3$ | OCH$_2$CF$_3$ | CH |
| H | H | H | H | H | CH$_3$ | OCF$_2$CF$_3$ | N |
| H | H | H | H | H | CH$_3$ | OCH$_2$CH$_2$OCH$_3$ | N |
| H | H | H | H | H | CH$_3$ | CH$_2$OCH$_3$ | CH |

TABLE 7

[In Formula I] Q is an oxazole with substituents R$_8$, R$_9$

| R$_1$ | R$_{13}$ | R$_9$ | R$_8$ | X | Y | Z |
|---|---|---|---|---|---|---|
| 5-F | H | H | H | CH$_3$ | CH$_3$ | N |
| 6-Cl | H | H | H | CH$_3$ | OCH$_3$ | N |
| 4-Br | H | H | H | OCH$_3$ | OCH$_3$ | N |
| 3-CH$_3$ | H | H | H | CH$_3$ | CH$_3$ | CH |
| 5-OCH$_3$ | H | H | H | CH$_3$ | OCH$_3$ | CH |
| 5-CF$_3$ | H | H | H | OCH$_3$ | OCH$_3$ | CH |
| H | CH$_3$ | H | H | CH$_3$ | CH$_3$ | N |

TABLE 7-continued

[In Formula I] Q is 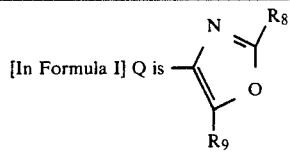

| R₁ | R₁₃ | R₉ | R₈ | X | Y | Z |
|---|---|---|---|---|---|---|
| H | CH₃ | H | H | CH₃ | OCH₃ | N |
| H | CH₃ | H | H | OCH₃ | OCH₃ | N |
| H | CH₃ | H | H | CH₃ | CH₃ | CH |
| H | CH₃ | H | H | OCH₃ | CH₃ | CH |
| H | CH₃ | H | H | OCH₃ | OCH₃ | CH |
| H | H | H | H | Cl | OCH₃ | CH |
| H | H | H | H | Cl | NH₂ | CH |
| H | H | H | H | Cl | NHCH₃ | CH |
| H | H | H | H | Cl | N(CH₃)₂ | CH |
| H | H | H | H | CH₃ | CH₂CH₃ | CH |
| H | H | H | H | OCH₃ | CH₂OCH₃ | N |
| H | H | H | H | CH₃ | OCH₂CH₃ | N |
| H | H | H | H | OCH₃ | OCH₂CH₃ | CH |
| H | H | H | H | CH₃ | CH(OCH₃)₂ | CH |
| H | H | H | H | CH₃ | CH₃ | N |
| H | H | H | H | OCH₃ | CH₃ | N |
| H | H | H | H | OCH₃ | OCH₃ | N |
| H | H | H | H | CH₃ | CH₃ | CH |
| H | H | H | H | OCH₃ | CH₃ | CH |
| H | H | H | H | OCH₃ | OCH₃ | CH |
| H | H | CH₃ | H | CH₃ | CH₃ | N |
| H | H | CH₃CH₂ | H | OCH₃ | CH₃ | N |
| H | H | H | CH₃ | OCH₃ | OCH₃ | N |
| H | H | H | CH₃CH₂ | CH₃ | CH₃ | CH |
| H | H | H | OCH₃ | OCH₃ | CH₃ | CH |
| H | H | H | OCH₂CH₃ | OCH₃ | OCH₃ | CH |
| H | H | H | SCH₃ | CH₃ | OCH₃ | N |
| H | H | H | Cl | OCH₃ | OCH₃ | N |
| H | H | H | Br | OCH₃ | CH₃ | CH |
| H | H | H | H | OCH₃ | SCH₃ | N |
| H | H | H | H | CH₃ | CF₃ | CH |
| H | H | H | H | CH₃ | OCH₂CF₃ | CH |
| H | H | H | H | CH₃ | OCF₂CF₃ | N |
| H | H | H | H | CH₃ | OCH₂CH₂OCH₃ | N |
| H | H | H | H | CH₃ | CH₂OCH₃ | CH |

TABLE 8

[In Formula I] Q is 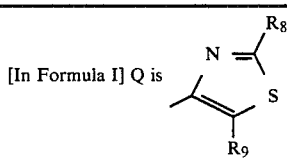

| R₁ | R₁₃ | R₉ | R₈ | X | Y | Z |
|---|---|---|---|---|---|---|
| 5-F | H | H | H | CH₃ | CH₃ | N |
| 6-Cl | H | H | H | CH₃ | OCH₃ | N |
| 4-Br | H | H | H | OCH₃ | OCH₃ | N |
| 3-CH₃ | H | H | H | CH₃ | CH₃ | CH |
| 5-OCH₃ | H | H | H | CH₃ | OCH₃ | CH |
| 5-CF₃ | H | H | H | OCH₃ | OCH₃ | CH |
| H | CH₃ | H | H | CH₃ | CH₃ | N |
| H | CH₃ | H | H | CH₃ | OCH₃ | N |
| H | CH₃ | H | H | OCH₃ | OCH₃ | N |
| H | CH₃ | H | H | CH₃ | CH₃ | CH |
| H | CH₃ | H | H | OCH₃ | CH₃ | CH |
| H | CH₃ | H | H | OCH₃ | OCH₃ | CH |
| H | H | H | H | Cl | OCH₃ | CH |
| H | H | H | H | Cl | NH₂ | CH |
| H | H | H | H | Cl | NHCH₃ | CH |
| H | H | H | H | CH₃ | CH₂CH₃ | CH |
| H | H | H | H | OCH₃ | CH₂OCH₃ | N |
| H | H | H | H | CH₃ | OCH₂CH₃ | N |
| H | H | H | H | OCH₃ | OCH₂CH₃ | CH |
| H | H | H | H | CH₃ | CH(OCH₃)₂ | CH |
| H | H | H | H | CH₃ | CH₃ | N |
| H | H | H | H | OCH₃ | CH₃ | N |
| H | H | H | H | OCH₃ | OCH₃ | N |
| H | H | H | H | CH₃ | CH₃ | CH |

TABLE 8-continued

[In Formula I] Q is $$\begin{array}{c} R_8 \\ N = \\ \\ \\ \\ R_9 \end{array} S$$

| R₁ | R₁₃ | R₉ | R₈ | X | Y | Z |
|---|---|---|---|---|---|---|
| H | H | H | H | OCH₃ | CH₃ | CH |
| H | H | H | H | OCH₃ | OCH₃ | CH |
| H | H | CH₃ | H | CH₃ | CH₃ | N |
| H | H | CH₃CH₂ | H | OCH₃ | CH₃ | N |
| H | H | H | CH₃ | OCH₃ | OCH₃ | N |
| H | H | H | CH₃CH₂ | CH₃ | CH₃ | CH |
| H | H | H | OCH₃ | OCH₃ | CH₃ | CH |
| H | H | H | OCH₂CH₃ | OCH₃ | OCH₃ | CH |
| H | H | H | SCH₃ | CH₃ | OCH₃ | N |
| H | H | H | Cl | OCH₃ | OCH₃ | N |
| H | H | H | Br | OCH₃ | CH₃ | CH |
| H | H | H | H | OCH₃ | SCH₃ | N |
| H | H | H | H | CH₃ | CF₃ | CH |
| H | H | H | H | CH₃ | OCH₂CF₃ | CH |
| H | H | H | H | CH₃ | OCF₂CF₃ | N |
| H | H | H | H | CH₃ | OCH₂CH₂OCH₃ | N |
| H | H | H | H | CH₃ | CH₂OCH₃ | CH |

TABLE 9

[In Formula I] Q is $$\begin{array}{c} R \\ | \\ N \\ \\ \\ R_9 \end{array} \begin{array}{c} R_8 \\ \\ \\ N \end{array}$$

| R | R₁ | R₁₃ | R₉ | R₈ | X | Y | Z |
|---|---|---|---|---|---|---|---|
| CH₃ | H | H | H | H | CH₃ | CH₃ | N |
| CH₃CH₂ | H | H | H | H | OCH₃ | CH₃ | N |
| CH₃CH₂CH₂ | H | H | H | H | OCH₃ | OCH₃ | N |
| (CH₃)₂CH | H | H | H | H | CH₃ | CH₃ | CH |
| CH₃CH₂CH₂CH₂ | H | H | H | H | OCH₃ | CH₃ | CH |
| (CH₃)₂CHCH₂— | H | H | H | H | OCH₃ | OCH₃ | CH |
| CH₃CHCH₂CH₃ | H | H | H | H | CH₃ | CH₃ | N |
| (CH₃)₃C | H | H | H | H | OCH₃ | CH₃ | N |
| H | H | H | H | H | OCH₃ | OCH₃ | N |
| CH₃ | 5-F | H | H | H | CH₃ | CH₃ | N |
| CH₃ | 6-Cl | H | H | H | CH₃ | OCH₃ | N |
| CH₃ | 4-Br | H | H | H | OCH₃ | OCH₃ | N |
| CH₃ | 3-CH₃ | H | H | H | CH₃ | CH₃ | CH |
| CH₃ | 5-OCH₃ | H | H | H | CH₃ | OCH₃ | CH |
| CH₃ | 5-CF₃ | H | H | H | OCH₃ | OCH₃ | CH |
| CH₃ | H | CH₃ | H | H | CH₃ | CH₃ | N |
| CH₃ | H | CH₃ | H | H | CH₃ | OCH₃ | N |
| CH₃ | H | CH₃ | H | H | OCH₃ | OCH₃ | N |
| CH₃ | H | CH₃ | H | H | CH₃ | CH₃ | CH |
| CH₃ | H | CH₃ | H | H | OCH₃ | CH₃ | CH |
| CH₃ | H | CH₃ | H | H | OCH₃ | OCH₃ | CH |
| CH₃ | H | H | H | H | Cl | OCH₃ | CH |
| CH₃ | H | H | H | H | Cl | NH₂ | CH |
| CH₃ | H | H | H | H | Cl | NHCH₃ | CH |
| CH₃ | H | H | H | H | Cl | NH(CH₃)₂ | CH |
| CH₃ | H | H | H | H | CH₃ | CH₂CH₃ | CH |
| CH₃ | H | H | H | H | OCH₃ | CH₂OCH₃ | N |
| H | CH₃ | H | H | H | CH₃ | OCH₂CH₃ | N |
| H | CH₃ | H | H | H | OCH₃ | OCH₂CH₃ | CH |
| H | CH₃ | H | H | H | CH₃ | CH(OCH₃)₂ | CH |
| H | CH₃ | H | H | H | CH₃ | CH₃ | N |
| H | CH₃ | H | H | H | OCH₃ | CH₃ | N |
| H | CH₃ | H | H | H | OCH₃ | OCH₃ | N |
| H | CH₃ | H | H | H | CH₃ | CH₃ | CH |
| H | CH₃ | H | H | H | OCH₃ | CH₃ | CH |
| H | CH₃ | H | H | H | OCH₃ | OCH₃ | CH |
| H | CH₃ | H | CH₃ | CH₃ | N | | |
| H | CH₃ | H | CH₃CH₂ | H | OCH₃ | CH₃ | N |
| H | CH₃ | H | H | CH₃ | OCH₃ | OCH₃ | N |
| H | CH₃ | H | H | CH₃CH₂ | CH₃ | CH₃ | CH |
| H | CH₃ | H | H | OCH₃ | OCH₃ | CH₃ | CH |

TABLE 9-continued

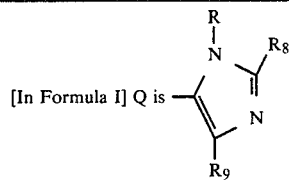

[In Formula I] Q is

| R | R1 | R13 | R9 | R8 | X | Y | Z |
|---|----|-----|----|----|---|---|---|
| H | CH3 | H | H | OCH2CH3 | OCH3 | OCH3 | CH |
| H | CH3 | H | H | SCH3 | CH3 | OCH3 | N |
| H | H | H | H | H | OCH3 | SCH3 | N |
| H | H | H | H | H | CH3 | CF3 | CH |
| H | H | H | H | H | CH3 | OCH2CF3 | CH |
| H | H | H | H | H | CH3 | OCF2CF3 | N |
| H | H | H | H | H | CH3 | OCH2CH2OCH3 | N |
| H | H | H | H | H | CH3 | CH2OCH3 | CH |

TABLE 10

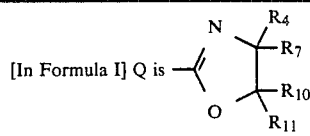

[In Formula I] Q is

| R1 | R4 | R7 | R10 | R11 | X | Y | Z |
|----|----|----|-----|-----|---|---|---|
| 5-F | H | H | H | H | OCH3 | OCH3 | N |
| 6-Cl | H | H | H | H | OCH3 | OCH3 | N |
| 4-Br | H | H | H | H | OCH3 | OCH3 | N |
| 3-CH3 | H | H | H | H | OCH3 | OCH3 | CH |
| 5-OCH3 | H | H | H | H | OCH3 | OCH3 | CH |
| 5-CF3 | H | H | H | H | OCH3 | OCH3 | CH |
| H | H | H | H | H | OCH3 | OCH3 | N |
| H | H | H | H | H | Cl | OCH3 | CH |
| H | H | H | H | H | Cl | OCH3 | N |
| H | H | H | H | H | OCH3 | OCH3 | CH |
| H | H | H | H | H | OCH3 | OCH2CH3 | N |
| H | H | H | H | H | OCH3 | OCH2CH3 | CH |
| H | CH3 | H | H | H | OCH3 | OCH3 | N |
| H | CH3 | H | H | H | OCH3 | OCH3 | CH |
| H | CH3 | CH3 | H | H | OCH3 | OCH3 | N |
| H | CH3 | CH3 | CH3 | H | OCH3 | OCH3 | N |
| H | CH3 | CH3 | CH3 | CH3 | OCH3 | OCH3 | CH |
| H | CH3CH2 | CH3 | CH3 | H | OCH3 | OCH3 | N |
| H | CH3CH2 | CH3CH2 | H | H | OCH3 | OCH3 | CH |
| H | H | H | CH3CH2 | CH3CH2 | OCH3 | OCH3 | N |
| H | CH3CH2CH2 | H | H | H | OCH3 | OCH3 | CH |
| H | H | CH3CH2CH2 | H | H | OCH3 | OCH3 | N |
| H | H | H | CH3CH2CH2 | H | OCH3 | OCH3 | CH |
| H | H | H | H | CH3CH2CH2 | OCH3 | OCH3 | N |
| H | CH3(CH2)3— | H | H | H | OCH3 | OCH3 | CH |
| H | H | CH3(CH2)3— | H | H | OCH3 | OCH3 | N |
| H | H | H | CH3(CH2)3— | H | OCH3 | OCH3 | CH |
| H | H | H | H | CH3(CH2)3— | OCH3 | OCH3 | N |
| H | (CH3)3C— | H | H | H | OCH3 | OCH3 | CH |
| H | H | (CH3)3C— | H | H | OCH3 | OCH3 | N |
| H | H | H | (CH3)3C— | H | OCH3 | OCH3 | CH |
| H | H | H | H | (CH3)3C— | OCH3 | OCH3 | N |
| H | CH3CHCH2CH3 | H | H | H | OCH3 | OCH3 | CH |
| H | H | (CH3)2CHCH2— | H | H | OCH3 | OCH3 | N |
| H | H | H | CH3CHCH2CH3 | H | OCH3 | OCH3 | CH |
| H | H | H | H | (CH3)2CHCH2— | OCH3 | OCH3 | N |
| H | CH3 | CH3 | H | H | OCH3 | OCH3 | CH |
| H | CH3 | CH3 | H | H | OCH3 | OCH3 | N |

TABLE 11

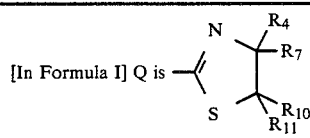

[In Formula I] Q is

| R1 | R4 | R7 | R10 | R11 | X | Y | Z |
|----|----|----|-----|-----|---|---|---|
| 5-F | H | H | H | H | OCH3 | OCH3 | N |

TABLE 11-continued

[In Formula I] Q is a group with N, R4, R7, S, R10, R11 substituents

| R1 | R4 | R7 | R10 | R11 | X | Y | Z |
|---|---|---|---|---|---|---|---|
| 6-Cl | H | H | H | H | OCH$_3$ | OCH$_3$ | N |
| 4-Br | H | H | H | H | OCH$_3$ | OCH$_3$ | N |
| 3-CH$_3$ | H | H | H | H | OCH$_3$ | OCH$_3$ | CH |
| 5-OCH$_3$ | H | H | H | H | OCH$_3$ | OCH$_3$ | CH |
| 5-CF$_3$ | H | H | H | H | OCH$_3$ | OCH$_3$ | CH |
| H | H | H | H | H | OCH$_3$ | OCH$_3$ | N |
| H | H | H | H | H | Cl | OCH$_3$ | CH |
| H | H | H | H | H | Cl | OCH$_3$ | N |
| H | H | H | H | H | OCH$_3$ | OCH$_3$ | CH |
| H | H | H | H | H | OCH$_3$ | OCH$_2$CH$_3$ | N |
| H | H | H | H | H | OCH$_3$ | OCH$_2$CH$_3$ | CH |
| H | CH$_3$ | H | H | H | OCH$_3$ | OCH$_3$ | N |
| H | CH$_3$ | CH$_3$ | H | H | OCH$_3$ | OCH$_3$ | CH |
| H | CH$_3$ | CH$_3$ | CH$_3$ | H | OCH$_3$ | OCH$_3$ | N |
| H | CH$_3$ | CH$_3$ | CH$_3$ | CH$_3$ | OCH$_3$ | OCH$_3$ | CH |
| H | CH$_3$CH$_2$ | CH$_3$ | CH$_3$ | H | OCH$_3$ | OCH$_3$ | N |
| H | CH$_3$CH$_2$ | CH$_3$CH$_2$ | H | H | OCH$_3$ | OCH$_3$ | CH |
| H | H | H | CH$_3$CH$_2$ | CH$_3$CH$_2$ | OCH$_3$ | OCH$_3$ | N |
| H | CH$_3$CH$_2$CH$_2$ | H | H | H | OCH$_3$ | OCH$_3$ | CH |
| H | H | CH$_3$CH$_2$CH$_2$ | H | H | OCH$_3$ | OCH$_3$ | N |
| H | H | H | CH$_3$CH$_2$CH$_2$ | H | OCH$_3$ | OCH$_3$ | CH |
| H | H | H | H | CH$_3$CH$_2$CH$_2$ | OCH$_3$ | OCH$_3$ | N |
| H | CH$_3$(CH$_2$)$_3$— | H | H | H | OCH$_3$ | OCH$_3$ | CH |
| H | H | CH$_3$(CH$_2$)$_3$— | H | H | OCH$_3$ | OCH$_3$ | N |
| H | H | H | CH$_3$(CH$_2$)$_3$— | H | OCH$_3$ | OCH$_3$ | CH |
| H | H | H | H | CH$_3$(CH$_2$)$_3$— | OCH$_3$ | OCH$_3$ | N |
| H | (CH$_3$)$_3$C— | H | H | H | OCH$_3$ | OCH$_3$ | CH |
| H | H | (CH$_3$)$_3$C— | H | H | OCH$_3$ | OCH$_3$ | N |
| H | H | H | (CH$_3$)$_3$C— | H | OCH$_3$ | OCH$_3$ | CH |
| H | H | H | H | (CH$_3$)$_3$C— | OCH$_3$ | OCH$_3$ | N |
| H | CH$_3$CHCH$_2$CH$_3$ | H | H | H | OCH$_3$ | OCH$_3$ | CH |
| H | H | (CH$_3$)$_2$CHCH$_2$— | H | H | OCH$_3$ | OCH$_3$ | N |
| H | H | H | CH$_3$CHCH$_2$CH$_3$ | H | OCH$_3$ | OCH$_3$ | CH |
| H | H | H | H | (CH$_3$)$_2$CHCH$_2$— | OCH$_3$ | OCH$_3$ | N |
| H | CH$_3$ | CH$_3$ | H | H | OCH$_3$ | OCH$_3$ | CH |
| H | CH$_3$ | CH$_3$ | H | H | OCH$_3$ | OCH$_3$ | N |

TABLE 12

[In Formula I] Q is a group with N, R4, R7, N-R, R10, R11 substituents

| R | R1 | R4 | R7 | R10 | R11 | X | Y | Z |
|---|---|---|---|---|---|---|---|---|
| CH$_3$ | H | H | H | H | H | OCH$_3$ | OCH$_3$ | CH |
| CH$_3$ | H | H | H | H | H | OCH$_3$ | OCH$_3$ | N |
| CH$_3$CH$_2$ | H | H | H | H | H | OCH$_3$ | OCH$_3$ | CH |
| CH$_3$CH$_2$CH$_2$ | H | H | H | H | H | OCH$_3$ | OCH$_3$ | N |
| CH$_3$(CH$_2$)$_3$ | H | H | H | H | H | OCH$_3$ | OCH$_3$ | CH |
| (CH$_3$)$_2$CH | H | H | H | H | H | OCH$_3$ | OCH$_3$ | N |
| (CH$_3$)$_2$CHCH$_2$— | H | H | H | H | H | OCH$_3$ | OCH$_3$ | CH |
| CH$_3$CHCH$_2$CH$_3$ | H | H | H | H | H | OCH$_3$ | OCH$_3$ | N |
| CH$_3$ | 5-F | H | H | H | H | OCH$_3$ | OCH$_3$ | N |
| CH$_3$ | 6-Cl | H | H | H | H | OCH$_3$ | OCH$_3$ | N |
| CH$_3$ | 4-Br | H | H | H | H | OCH$_3$ | OCH$_3$ | N |
| CH$_3$ | 3-CH$_3$ | H | H | H | H | OCH$_3$ | OCH$_3$ | CH |
| CH$_3$ | 5-OCH$_3$ | H | H | H | H | OCH$_3$ | OCH$_3$ | CH |
| CH$_3$ | 5-CF$_3$ | H | H | H | H | OCH$_3$ | OCH$_3$ | CH |
| CH$_3$ | H | H | H | H | H | OCH$_3$ | OCH$_3$ | N |
| CH$_3$ | H | H | H | H | H | Cl | OCH$_3$ | CH |
| CH$_3$ | H | H | H | H | H | Cl | OCH$_3$ | N |
| CH$_3$ | H | H | H | H | H | OCH$_3$ | OCH$_3$ | CH |
| CH$_3$ | H | H | H | H | H | OCH$_3$ | OCH$_2$CH$_3$ | N |
| CH$_3$ | H | H | H | H | H | OCH$_3$ | OCH$_2$CH$_3$ | CH |
| CH$_3$ | H | CH$_3$ | H | H | H | OCH$_3$ | OCH$_3$ | N |
| CH$_3$ | H | CH$_3$ | CH$_3$ | H | H | OCH$_3$ | OCH$_3$ | CH |
| CH$_3$ | H | CH$_3$ | CH$_3$ | CH$_3$ | H | OCH$_3$ | OCH$_3$ | N |
| CH$_3$ | H | CH$_3$ | CH$_3$ | CH$_3$ | CH$_3$ | OCH$_3$ | OCH$_3$ | CH |

TABLE 12-continued

[In Formula I] Q is 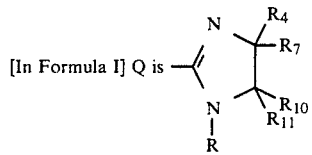

| R | R₁ | R₄ | R₇ | R₁₀ | R₁₁ | X | Y | Z |
|---|---|---|---|---|---|---|---|---|
| CH₃ | H | CH₃CH₂ | CH₃ | CH₃ | H | OCH₃ | OCH₃ | N |
| CH₃ | H | CH₃CH₂ | CH₃CH₂ | H | H | OCH₃ | OCH₃ | CH |
| CH₃ | H | H | H | CH₃CH₂ | CH₃CH₂ | OCH₃ | OCH₃ | N |
| CH₃ | H | CH₃CH₂CH₂ | H | H | H | OCH₃ | OCH₃ | CH |
| CH₃ | H | H | CH₃CH₂CH₂ | H | H | OCH₃ | OCH₃ | N |
| CH₃ | H | H | H | CH₃CH₂CH₂ | H | OCH₃ | OCH₃ | CH |
| CH₃ | H | H | H | H | CH₃CH₂CH₂ | OCH₃ | OCH₃ | N |
| CH₃ | H | CH₃(CH₂)₃— | H | H | H | OCH₃ | OCH₃ | CH |
| CH₃ | H | H | CH₃(CH₂)₃— | H | H | OCH₃ | OCH₃ | N |
| CH₃ | H | H | H | CH₃(CH₂)₃— | H | OCH₃ | OCH₃ | CH |
| CH₃ | H | H | H | H | CH₃(CH₂)₃— | OCH₃ | OCH₃ | N |
| CH₃ | H | (CH₃)₃C— | H | H | H | OCH₃ | OCH₃ | CH |
| CH₃ | H | H | (CH₃)₃C— | H | H | OCH₃ | OCH₃ | N |
| CH₃ | H | H | H | (CH₃)₃C— | H | OCH₃ | OCH₃ | CH |
| CH₃ | H | H | H | H | (CH₃)₃C— | OCH₃ | OCH₃ | N |
| CH₃ | H | CH₃CHCH₂CH₃ | H | H | H | OCH₃ | OCH₃ | CH |
| CH₃ | H | H | (CH₃)₂CHCH₂— | H | H | OCH₃ | OCH₃ | N |
| CH₃ | H | H | H | CH₃CHCH₂CH₃ | H | OCH₃ | OCH₃ | CH |
| CH₃ | H | H | H | H | (CH₃)₂CHCH₂— | OCH₃ | OCH₃ | N |
| CH₃ | H | CH₃ | CH₃ | H | H | OCH₃ | OCH₃ | CH |
| CH₃ | H | CH₃ | CH₃ | H | H | OCH₃ | OCH₃ | N |

TABLE 13

[In Formula I] Q is 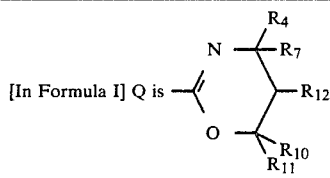

| R₁ | R₄ | R₇ | R₁₀ | R₁₁ | R₁₂ | X | Y | Z |
|---|---|---|---|---|---|---|---|---|
| 5-F | H | H | H | H | H | OCH₃ | OCH₃ | N |
| 6-Cl | H | H | H | H | H | OCH₃ | OCH₃ | N |
| 4-Br | H | H | H | H | H | OCH₃ | OCH₃ | N |
| 3-CH₃ | H | H | H | H | H | OCH₃ | OCH₃ | CH |
| 5-OCH₃ | H | H | H | H | H | OCH₃ | OCH₃ | CH |
| 5-CH₃ | H | H | H | H | H | OCH₃ | OCH₃ | CH |
| H | H | H | H | H | H | OCH₃ | OCH₃ | CH |
| H | H | H | H | H | H | Cl | OCH₃ | CH |
| H | H | H | H | H | H | Cl | OCH₃ | N |
| H | H | H | H | H | H | OCH₃ | OCH₃ | N |
| H | CH₃ | H | H | H | H | OCH₃ | OCH₂CH₃ | CH |
| H | H | CH₃ | H | H | H | OCH₃ | OCH₂CH₃ | N |
| H | H | H | CH₃ | H | H | OCH₃ | OCH₃ | CH |
| H | H | H | H | CH₃ | H | OCH₃ | OCH₃ | N |
| H | H | H | H | H | CH₃ | OCH₃ | OCH₃ | CH |
| H | CH₃CH₂ | CH₃ | CH₃ | H | H | OCH₃ | OCH₃ | N |
| H | CH₃CH₂ | CH₃CH₂ | H | H | H | OCH₃ | OCH₃ | CH |
| H | H | H | CH₃CH₂ | CH₃CH₂ | H | OCH₃ | OCH₃ | N |
| H | CH₃CH₂CH₂ | H | H | H | H | OCH₃ | OCH₃ | CH |
| H | H | CH₃CH₂CH₂ | H | H | H | OCH₃ | OCH₃ | N |
| H | H | H | CH₃CH₂CH₂ | H | H | OCH₃ | OCH₃ | CH |
| H | H | H | H | CH₃CH₂CH₂ | H | OCH₃ | OCH₃ | N |
| H | CH₃(CH₂)₃ | H | H | H | H | OCH₃ | OCH₃ | CH |
| H | H | CH₃CHCH₂CH₃ | H | H | H | OCH₃ | OCH₃ | N |
| H | H | H | (CH₃)₂CHCH₂ | H | H | OCH₃ | OCH₃ | CH |
| H | H | H | H | (CH₃)₃C— | H | OCH₃ | OCH₃ | N |
| H | CH₃ | CH₃ | H | H | H | OCH₃ | OCH₃ | CH |
| H | CH₃ | CH₃ | H | H | H | OCH₃ | OCH₃ | N |

TABLE 14

[In Formula I] Q is 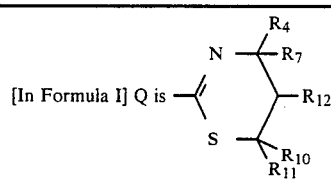

| R₁ | R₄ | R₇ | R₁₀ | R₁₁ | R₁₂ | X | Y | Z |
|---|---|---|---|---|---|---|---|---|
| 5-F | H | H | H | H | H | OCH₃ | OCH₃ | N |
| 6-Cl | H | H | H | H | H | OCH₃ | OCH₃ | N |
| 4-Br | H | H | H | H | H | OCH₃ | OCH₃ | N |
| 3-CH₃ | H | H | H | H | H | OCH₃ | OCH₃ | CH |
| 5-OCH₃ | H | H | H | H | H | OCH₃ | OCH₃ | CH |
| 5-CH₃ | H | H | H | H | H | OCH₃ | OCH₃ | CH |
| H | H | H | H | H | H | OCH₃ | OCH₃ | CH |
| H | H | H | H | H | H | Cl | OCH₃ | CH |
| H | H | H | H | H | H | Cl | OCH₃ | N |
| H | H | H | H | H | H | OCH₃ | OCH₃ | N |
| H | CH₃ | H | H | H | H | OCH₃ | OCH₂CH₃ | CH |
| H | H | CH₃ | H | H | H | OCH₃ | OCH₂CH₃ | N |
| H | H | H | CH₃ | H | H | OCH₃ | OCH₃ | CH |
| H | H | H | H | CH₃ | H | OCH₃ | OCH₃ | N |
| H | H | H | H | H | CH₃ | OCH₃ | OCH₃ | CH |
| H | CH₃CH₂ | CH₃ | CH₃ | H | H | OCH₃ | OCH₃ | N |
| H | CH₃CH₂ | CH₃CH₂ | H | H | H | OCH₃ | OCH₃ | CH |
| H | H | H | CH₃CH₂ | CH₃CH₂ | H | OCH₃ | OCH₃ | N |
| H | CH₃CH₂CH₂ | H | H | H | H | OCH₃ | OCH₃ | CH |
| H | H | CH₃CH₂CH₂ | H | H | H | OCH₃ | OCH₃ | N |
| H | H | H | CH₃CH₂CH₂ | H | H | OCH₃ | OCH₃ | CH |
| H | H | H | H | CH₃CH₂CH₂ | H | OCH₃ | OCH₃ | N |
| H | CH₃(CH₂)₃ | H | H | H | H | OCH₃ | OCH₃ | CH |
| H | H | CH₃CHCH₂CH₃ | H | H | H | OCH₃ | OCH₃ | N |
| H | H | H | (CH₃)₂CHCH₂ | H | H | OCH₃ | OCH₃ | CH |
| H | H | H | H | (CH₃)₃C— | H | OCH₃ | OCH₃ | N |
| H | CH₃ | CH₃ | H | H | H | OCH₃ | OCH₃ | CH |
| H | CH₃ | CH₃ | H | H | H | OCH₃ | OCH₃ | N |

TABLE 15

[In Formula I] Q is 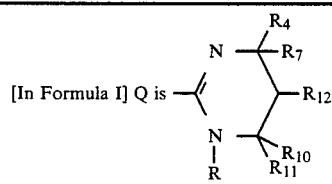

| R | R₁ | R₄ | R₇ | R₁₀ | R₁₁ | R₁₂ | X | Y | Z |
|---|---|---|---|---|---|---|---|---|---|
| CH₃ | H | H | H | H | H | H | OCH₃ | OCH₃ | N |
| CH₃CH₂ | H | H | H | H | H | H | OCH₃ | OCH₃ | CH |
| CH₃CH₂CH₂ | H | H | H | H | H | H | OCH₃ | OCH₃ | N |
| (CH₃)₂CH | H | H | H | H | H | H | OCH₃ | OCH₃ | CH |
| CH₃(CH₂)₃ | H | H | H | H | H | H | OCH₃ | OCH₃ | N |
| (CH₃)₂CHCH₂— | H | H | H | H | H | H | OCH₃ | OCH₃ | CH |
| CH₃CHCH₂CH₃ | H | H | H | H | H | H | OCH₃ | OCH₃ | N |
| (CH₃)₃C | H | H | H | H | H | H | OCH₃ | OCH₃ | CH |
| CH₃ | 5-F | H | H | H | H | H | OCH₃ | OCH₃ | N |
| CH₃ | 6-Cl | H | H | H | H | H | OCH₃ | OCH₃ | N |
| CH₃ | 4-Br | H | H | H | H | H | OCH₃ | OCH₃ | N |
| CH₃ | 3-CH₃ | H | H | H | H | H | OCH₃ | OCH₃ | CH |
| CH₃ | 5-OCH₃ | H | H | H | H | H | OCH₃ | OCH₃ | CH |
| CH₃ | 5-CF₃ | H | H | H | H | H | OCH₃ | OCH₃ | CH |
| CH₃ | H | H | H | H | H | H | OCH₃ | OCH₃ | N |
| CH₃ | H | H | H | H | H | H | Cl | OCH₃ | CH |
| CH₃ | H | H | H | H | H | H | Cl | OCH₃ | N |
| CH₃ | H | H | H | H | H | H | OCH₃ | OCH₃ | CH |
| CH₃ | H | H | H | H | H | H | OCH₃ | OCH₂CH₃ | N |
| CH₃ | H | H | H | H | H | H | OCH₃ | OCH₂CH₃ | CH |
| CH₃ | H | CH₃ | H | H | H | H | OCH₃ | OCH₃ | N |
| CH₃ | H | CH₃ | CH₃ | H | H | H | OCH₃ | OCH₃ | CH |
| CH₃ | H | CH₃ | CH₃ | CH₃ | H | H | OCH₃ | OCH₃ | N |
| CH₃ | H | CH₃ | CH₃ | CH₃ | CH₃ | H | OCH₃ | OCH₃ | H |
| CH₃ | H | CH₃CH₂ | CH₃ | CH₃ | H | H | OCH₃ | OCH₃ | N |
| CH₃ | H | CH₃CH₂ | CH₃CH₂ | H | H | H | OCH₃ | OCH₃ | CH |
| CH₃ | H | H | H | CH₃CH₂ | CH₃CH₂ | H | OCH₃ | OCH₃ | N |
| CH₃ | H | CH₃CH₂CH₂ | H | H | H | H | OCH₃ | OCH₃ | CH |
| CH₃ | H | H | CH₃CH₂CH₂ | H | H | H | OCH₃ | OCH₃ | N |

TABLE 15-continued

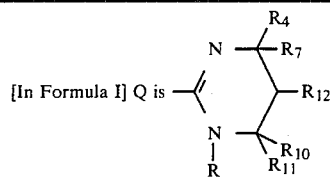

[In Formula I] Q is

| R | R₁ | R₄ | R₇ | R₁₀ | R₁₁ | R₁₂ | X | Y | Z |
|---|----|----|----|-----|-----|-----|---|---|---|
| CH₃ | H | H | H | CH₃CH₂CH₂ | H | H | OCH₃ | OCH₃ | CH |
| CH₃ | H | H | H | H | CH₃CH₂CH₂ | H | OCH₃ | OCH₃ | N |
| CH₃ | H | CH₃(CH₂)₃— | H | H | H | H | OCH₃ | OCH₃ | CH |
| CH₃ | H | H | CH₃(CH₂)₃— | H | H | H | OCH₃ | OCH₃ | N |
| CH₃ | H | H | H | CH₃(CH₂)₃— | H | H | OCH₃ | OCH₃ | CH |
| CH₃ | H | H | H | H | CH₃(CH₂)₃— | H | OCH₃ | OCH₃ | N |
| CH₃ | H | (CH₃)₃C— | H | H | H | H | OCH₃ | OCH₃ | CH |
| CH₃ | H | H | (CH₃)₃C— | H | H | H | OCH₃ | OCH₃ | N |
| CH₃ | H | H | H | (CH₃)₃C— | H | H | OCH₃ | OCH₃ | CH |
| CH₃ | H | H | H | H | (CH₃)₃C— | H | OCH₃ | OCH₃ | N |
| CH₃ | H | CH₃CHCH₂CH₃ | H | H | H | H | OCH₃ | OCH₃ | CH |
| CH₃ | H | H | (CH₃)₂CHCH₂— | H | H | H | OCH₃ | OCH₃ | N |
| CH₃ | H | H | H | CH₃CHCH₂CH₃ | H | H | OCH₃ | OCH₃ | CH |
| CH₃ | H | H | H | H | (CH₃)₂CHCH₂— | H | OCH₃ | OCH₃ | N |
| CH₃ | H | CH₃ | CH₃ | H | H | H | OCH₃ | OCH₃ | CH |
| CH₃ | H | CH₃ | CH₃ | H | H | H | OCH₃ | OCH₃ | N |
| CH₃ | H | H | H | H | H | CH₃ | OCH₃ | OCH₃ | CH |

TABLE 16

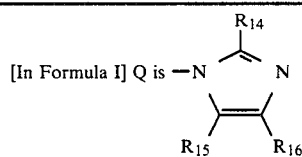

[In Formula I] Q is

| R₁ | R₁₃ | R₁₄ | R₁₅ | R₁₆ | X | Y | Z |
|----|-----|-----|-----|-----|---|---|---|
| 5-F | H | H | H | H | CH₃ | CH₃ | N |
| 6-Cl | H | H | H | H | CH₃ | OCH₃ | N |
| 4-Br | H | H | H | H | OCH₃ | OCH₃ | N |
| 3-CH₃ | H | H | H | H | CH₃ | CH₃ | CH |
| 5-OCH₃ | H | H | H | H | CH₃ | OCH₃ | CH |
| 5-CF₃ | H | H | H | H | OCH₃ | OCH₃ | CH |
| H | H | H | H | H | Cl | OCH₃ | CH |
| H | H | H | H | H | Cl | NH₂ | CH |
| H | H | H | H | H | Cl | NHCH₃ | CH |
| H | H | H | H | H | Cl | N(CH₃)₂ | CH |
| H | H | H | H | H | CH₃ | CH₂CH₃ | CH |
| H | H | H | H | H | OCH₃ | CH₂OCH₃ | N |
| H | H | H | H | H | CH₃ | OCH₂CH₃ | N |
| H | H | H | H | H | OCH₃ | OCH₂CH₃ | CH |
| H | H | H | H | H | CH₃ | CH(OCH₃)₂ | CH |
| H | CH₃ | H | H | H | CH₃ | CH₃ | CH |
| H | CH₃ | H | H | H | CH₃ | OCH₃ | CH |
| H | CH₃ | H | H | H | OCH₃ | OCH₃ | CH |
| H | CH₃ | H | H | H | CH₃ | CH₃ | N |
| H | CH₃ | H | H | H | OCH₃ | CH₃ | N |
| H | CH₃ | H | H | H | OCH₃ | OCH₃ | N |
| H | H | CH₃ | H | H | CH₃ | CH₃ | CH |
| H | H | CH₃CH₂ | H | H | CH₃ | OCH₃ | CH |
| H | H | CH₃O | H | H | OCH₃ | OCH₃ | CH |
| H | H | CH₃CH₂O | H | H | CH₃ | OCH₃ | N |
| H | H | CH₃S | H | H | CH₃ | OCH₃ | N |
| H | H | Cl | H | H | OCH₃ | OCH₃ | N |
| H | H | Br | H | H | OCH₃ | OCH₃ | N |
| H | H | H | CH₃ | H | CH₃ | CH₃ | CH |
| H | H | H | H | CH₃ | CH₃ | OCH₃ | CH |
| H | H | H | CH₃ | CH₃ | OCH₃ | OCH₃ | CH |
| H | H | H | CH₃CH₂ | H | CH₃ | OCH₃ | N |
| H | H | H | H | CH₃CH₂ | OCH₃ | OCH₃ | N |
| H | H | H | H | H | CH₃ | CH₃ | N |
| H | H | H | H | H | CH₃ | OCH₃ | N |
| H | H | H | H | H | OCH₃ | OCH₃ | N |
| H | H | H | H | H | CH₃ | CH₃ | CH |
| H | H | H | H | H | CH₃ | OCH₃ | CH |
| H | H | H | H | H | OCH₃ | OCH₃ | CH |

TABLE 17

Structure: Benzene ring with Q substituent and SO₂NHC(=W″)N(R₁₃)—A group, with R₁ substituent.

| Q | W″ | R₁ | R₁₃ | A |
|---|----|----|----|---|
| oxazol-2-yl (O top) | O | H | H | 4-methyl-furo-pyrimidine (CH₃, fused O ring) |
| oxazol-2-yl | O | H | H | 4-methoxy-furo-pyrimidine (OCH₃) |
| oxazol-2-yl | O | H | H | 4-methyl-cyclopenta-pyrimidine (CH₃) |
| thiazol-2-yl | O | H | H | 4-methoxy-cyclopenta-pyrimidine (OCH₃) |
| thiazol-2-yl | O | H | H | 4-methyl-furo-pyrimidine with =C(CH₃)- (CH₃) |
| oxazol-2-yl | O | H | H | 4-methoxy-furo-pyrimidine with =C(CH₃)- (OCH₃) |

TABLE 18

Structure: Benzene ring with Q substituent and SO₂NHC(=W‴)N(R₁₃)— attached to 1,2,4-triazole with X₂ and Y₂ substituents; R₁ substituent on ring.

| Q | W‴ | R₁ | R₁₃ | X₂ | Y₂ |
|---|-----|----|----|----|----|
| oxazol-2-yl | O | H | H | CH₃ | OCH₃ |
| thiazol-2-yl | O | H | H | CH₃ | OCH₃ |
| 1-methyl-imidazol-2-yl | O | H | H | CH₃ | OCH₃ |
| N-methyl-imidazol-yl (CH₃ on N) | O | H | H | CH₃ | OCH₃ |
| oxazolyl (N=CH—O) | O | H | H | CH₃ | OCH₃ |
| thiazolyl (N=CH—S) | O | H | H | CH₃ | OCH₃ |
| imidazolyl (N=CH—N—R) | O | H | H | CH₃ | OCH₃ |
| thiazolyl (S—CH=N) | O | H | H | CH₃ | OCH₃ |
| oxazolyl (O—CH=N) | O | H | H | CH₃ | OCH₃ |
| imidazol-1-yl | O | H | H | CH₃ | OCH₃ |
| 2-methyl-pyrrol-1-yl | O | H | H | CH₃ | OCH₃ |
| imidazol-1-yl | O | H | H | CH₃ | OCH₂CH₃ |
| imidazol-1-yl | O | H | H | CH₃ | CH₃S |

TABLE 18-continued $$\text{structure with } Q, R_1, SO_2NHC(W'')N(R_{13})-\text{pyrazole with } X_2, Y_2$$

| Q | W''' | $R_1$ | $R_{13}$ | $X_2$ | $Y_2$ |
|---|---|---|---|---|---|
| -N(pyrazol-1-yl) | O | H | H | $CH_3$ | $CH_3CH_2S$ |
| -N(3-methylpyrazol-1-yl) | O | H | H | $CH_3CH_2$ | $OCH_3$ |
| N-(oxazol-2-yl) | O | H | H | $CH_3CH_2CH_3$ | $OCH_3$ |
| N-(oxazol-2-yl) | O | H | H | $(CH_3)_2CH$ | $OCH_3$ |
| N-(oxazol-2-yl) | O | H | H | $CF_3CH_2$ | $OCH_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 19

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are somtimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 12

Wettable Powder

| | |
|---|---|
| N—[(4,6-dimethoxypyrimidin-2-yl)aminocarbonyl]-2-(1-methyl-1H—imidazol-2-yl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 13

Wettable Powder

| | |
|---|---|
| N—[(4,6-dimethylpyrimidin-2-yl)aminocarbonyl]-2-(1-methyl-1H—imidazol-2-yl)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 14

Granule

| | |
|---|---|
| Wettable Powder of Example 13 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 15

Extruded Pellet

| | |
|---|---|
| N—[(4-methoxy-6-methylpyrimidin-2-yl)aminocarbonyl]-2-(1-methyl-1H—imidazol-2-yl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produde pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 16

Oil Suspension

| | |
|---|---|
| N—[(4,6-dimethoxypyrimidin-2-yl)aminocarbonyl]-2-(oxazol-2-yl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 17

Wettable Powder

| | |
|---|---|
| N—[(4,6-dimethylpyrimidin-2-yl)aminocarbonyl]-2-oxazol-2-yl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 18

Low Strength Granule

| | |
|---|---|
| N—[(4,6-dimethyl-1,3,5-triazin-2-yl)aminocarbonyl]-2-(oxazol-2-yl)benzenesulfomamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 19

Aqueous Suspension

| | |
|---|---|
| N—[(4-methoxy-methylpyrimidin-2-yl)aminocarbonyl]-2-(oxazol-2-yl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 57.6% |

The ingredients are blended and ground together in a sand mill to produce particles essentially all under 5 microns in size.

EXAMPLE 20

Solution

| | |
|---|---|
| N—[(4,6-dimethoxy-1,3,5-triazin-2-yl)aminocarbonyl]-2-(oxazol-2-yl)benzenesulfonamide, sodium salt | 5% |
| water | 95% |

The salt is added directly to the water with stirring to produce the solution, which may then be packaged for use.

EXAMPLE 21

Low Strength Granule

| | |
|---|---|
| 2-(4,5-dihydro-4,4-dimethyloxazol-2-yl)-N—[(4,6-dimethoxy-1,3,5-triazin-2-yl)aminocarbonyl]-benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the

EXAMPLE 22

Granule

| | |
|---|---|
| N—[(4-methoxy-6-methyl-1,3,5-triazin-2-yl)aminocarbonyl]-2-(oxazol-2-yl)benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 23

High Strength Concentrate

| | |
|---|---|
| N—[(4,6-dimethoxypyrimidin-2-yl)aminocarbonyl]-2-(1-methyl-1H—imidazol-2-yl)benzenesulfonamide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 24

Wettable Powder

| | |
|---|---|
| N—[(4,6-dimethylpyrimidin-2-yl)aminocarbonyl]-2-(1-methyl-1H—imidazol-2-yl)benzenesulfonamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 25

Wettable Powder

| | |
|---|---|
| N—[(4,6-dimethylpyrimidin-2-yl)aminocarbonyl]-2-(oxazol-2-yl)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 26

Oil Suspension

| | |
|---|---|
| N—[(4,6-dimethoxy-1,3,5-triazin-2-yl)aminocarbonyl]-2-(oxazol-2-yl)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drivein theaters, around billboards, highway and railroad structures. Alternatively, some of the subject compounds are useful for selective pre- and/or post-emergence weed control in crops, such as wheat and barley.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow:

Compound Structures

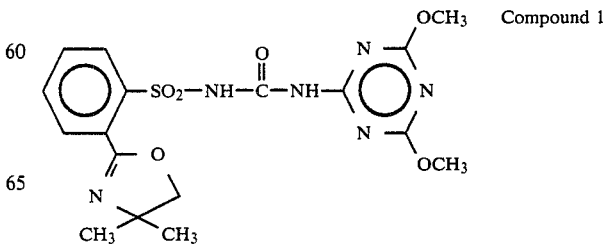

Compound 1

-continued
Compound Structures

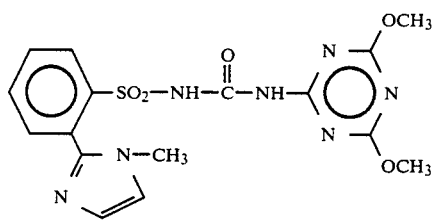 Compound 2

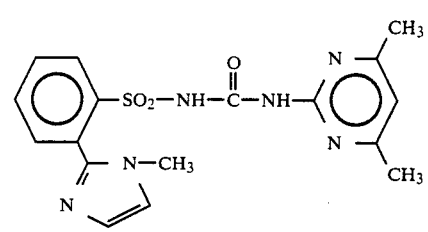 Compound 3

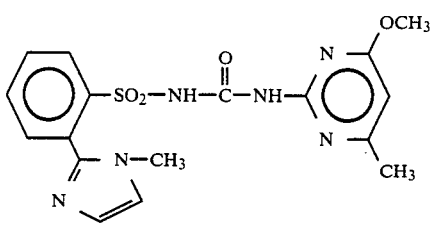 Compound 4

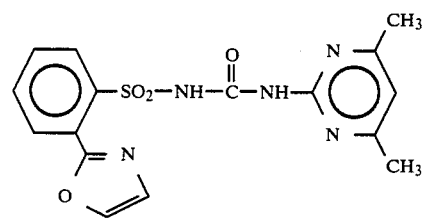 Compound 5

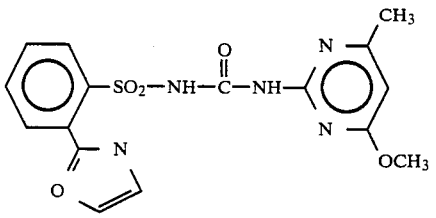 Compound 6

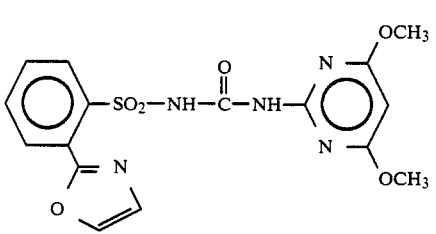 Compound 7

-continued
Compound Structures

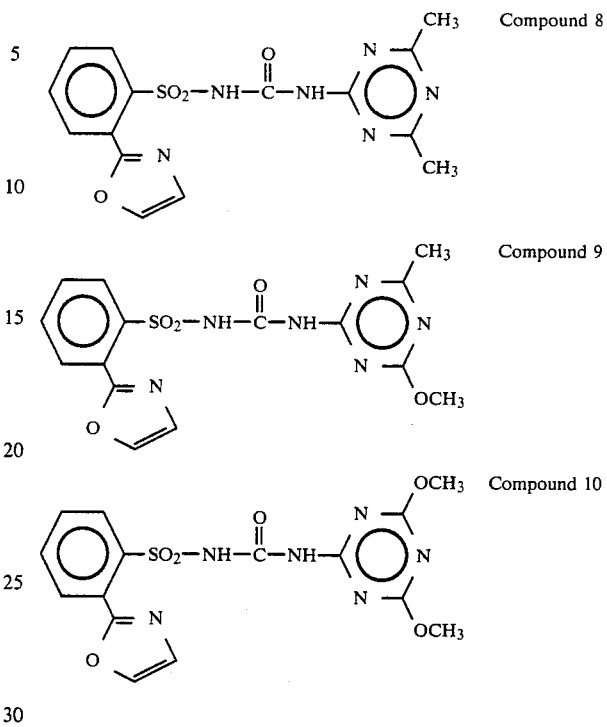

Test A

Seeds of crabgrass (Digitaria sp.), barnyardgrass (Echinochloa crusgalli), wild oats (Avena fatua), cassia (Cassia tora), morningglory (Ipomoea sp.), cocklebur (Xanthium sp.), sorghum, corn, soybean, rice, wheat and nutsedge tubers (Cyperus rotundus) were planted in a growth medium and treated pre-emergence with the chemicals dissolved in a non-phytotoxic solvent solution of the compounds of Table A. At the same time, cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed with a non-phytotoxic solvent solution of the compounds of Table A. Other containers of the above mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0=no effect;
10=maximum effect;
C=chlorosis and/or necrosis;
D=defoliation;
E=emergence inhibition;
G=growth retardation;
H=formative effects;
U=unusual pigmentation;
X=axillary stimulation; and
6Y=abscised buds or flowers.

The data indicate that the compounds tested are highly active herbicides. Certain of the compounds have utility for selective weed control in wheat.

TABLE A

| Rate kg/ha | Cmpd. 1 0.4 | Cmpd. 2 0.4 | Cmpd. 2 0.05 | Cmpd. 3 0.4 | Cmpd. 3 0.05 | Cmpd. 4 0.4 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 |
|---|---|---|---|---|---|---|---|---|---|---|---|---|---|
| POST-EMERGENCE | | | | | | | | | | | | | |
| Bush bean | 9C | 9D,9G,6Y | 7C,9G,6Y | 4C,5C | 1C | 6C,8G,6Y | 4C,8G,6Y | 4C,9G,6Y | 9C | 9C | 3C,9G,6Y | 9C | 9C |
| Cotton | 5C,9C | 7C,9G | 5C,5H,9G | 2C | 0 | 4C,5H | 2C | 5C,9G | 6C,9C | 5C,9H | 3C,7H | 6C,9G | 5C,9G |
| Morningglory | 6C,9G | 5C,9G | 5C,9G | 2C,3H | 2C | 2C,7G | 3C,7H | 3C,9G | 9C | 6C,9G | 4C,9G | 9C | 9C |
| Cocklebur | 5C,9G | 2C,6G | 2C,5G | 1C | 0 | 4C,8G | 1C | 5C,9G | 9C | 9C | 2C,8H | 9C | 9C |
| Cassia | 5C,9G | 3C,7G | 3C,7C | 2C | 0 | 4C,4H | 1C | 5C,8G | 9C | 9C | 4C,5H | 9C | 9C |
| Nutsedge | 5G | 2C,7G | 1C,8G | 0 | 0 | 2C,8G | 2G | 1C,3H | 2C,7G | 2C,8G | 2C,5G,5X | 1C,5G | 3C,8G |
| Crabgrass | 1C | 3C,7G | 3C,7G | 2G | 0 | 2C,5G | 2G | 9C | 9C | 6C,9H | 1C | 1C,5G | 1C,2H |
| Barnyardgrass | 3C,8H | 9C | 5C,9H | 2C,4G | 0 | 4C,9H | 3H | 2C,9H | 9C | 2C,9G | 3C,7H | 4C,6H | 3C,9H |
| Wild Oats | 0 | 4C,9G | 3C,8H | 2C,6G | 0 | 2C,9G | 1H | 9C | 2C,9H | 9C | 2C,7G | 3C | 1C,4G |
| Wheat | 0 | 3C,9G | 9G | 1C,5G | 0 | 1C,8H | 1H | 2C,9G | 9C | 3C,9G | 0 | 0 | 0 |
| Corn | 3C,9H | 2C,7H | 2C,5H | 0 | 1C | 2C,3H | 2G | 6U,9G | 6U,9G | 6U,9G | 2U,8G | 4U,9G | 2C,8H |
| Soybean | 3C,9G | 4C,9G | 3C,8G | 2C,3H | 0 | 3C,8G | 2C,4H | 4C,9G | 9C | 9C | 3C,8C | 6C,9G | 9C |
| Rice | 3C,8C | 5C,9G | 6C,8G | 6C,8G | 2C,6G | 4C,9G | 5C,7G | 5C,9G | 5C,9G | 5C,9C | 5C,9C | 2C,8G | 6G |
| Sorghum | 2C,9G | 6C,9G | 4C,9C | 2C,5G | 0 | 4C,8H | 2C,5G | 3U,9G | 5U,9H | 6U,9C | 2C,7H | 1C,9H | 1C,8H |
| PRE-EMERGENCE | | | | | | | | | | | | | |
| Morningglory | 9G | 8H | 2C,9G | 3C,7H | 0 | 2C,9G | 4C | 7G | 2C,9G | 9H | 8H | 9H | 9C |
| Cocklebur | 9G | 9H | 9H | 2C,5G | 0 | 2C,9H | 7G | 8H | 9H | — | 9H | 8H | 3C,9H |
| Cassia | 9G | 3C,8G | 2C,6G | 3C | 0 | 2C | 3C | 3C,7G | 2C,9G | 3C,9G | 2C,5H | 5C,9G | 2C,9G |
| Nutsedge | 9G | 2C,8G | 6G | 0 | 0 | 2C,5G | 2G | 9G | 10E | 10E | 0 | 5G | 8G |
| Crabgrass | 2G | 7C,9C | 5C,8G | 1C | 0 | 4G,7G | 2C | 2C | 2C,7G | 2C,8G | 0 | 1C,5H | 1C |
| Barnyardgrass | 4C,9H | 7C,9H | 7C,9H | 3C | 0 | 3C,6H | 2C | 2C,7H | 6C,9H | 6C,9H | 1C | 2C,8G | 4C,7H |
| Wild Oats | 5G | 6C,9H | 6C,9H | 0 | 0 | 3C,8H | 2C,6G | 2C,9G | 5C,9G | 2C,6G | 2C,6G | 2C | 1C,8G |
| Wheat | 0 | 5C,9H | 5C,9H | 0 | 0 | 3C,8G | 1C | 2C,7G | 2C,9H | 1C,8G | 0 | 0 | 1C |
| Corn | 2C,8G | 5C,9H | 6C,9H | 1C,5G | 0 | 3C,6G | 2C | 1C,8G | 9H | 2U,9H | 2C | 2C,8G | 2C,8H |
| Soybean | 2C,8H | 4C,6H | 4C,5H | 1C | 0 | 4C | 1C | 2C,6H | 9H | 9H | 2C | 3C,8H | 9H |
| Rice | 2C,8G | 10E | 9H | 1C,3G | 0 | 5C,9H | 3C | 2C,8G | 10E | 10E | 2C | 2C,7G | 3C,8G |
| Sorghum | 2C,7G | 5C,9H | 6C,9H | 1C | 0 | 4C,8G | 2C | 2C,9H | 10H | 10H | 2C | 2C,8H | 2C,8H |

Test B

Two plastic bulb pans were filled with either Fallsington silt loam or Woodstown sandy loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

ton silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), *Galium aparine*, tumble mustard (*Sisymbrium altissium*) kochia (*Kochia scoparia*), shepherd's purse (*Capsella bursa-pastoris*), *Matricaria inodora*, black nightshade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The compounds applied were diluted with a nonphytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C. It will be noted that the compounds tested have utility for selective pre- and post-emergence weed control in wheat and barley.

TABLE B

| | PRE-EMERGENCE ON | | | | | | | | | | | |
|---|---|---|---|---|---|---|---|---|---|---|---|---|
| | Fallsington Silt Loam Soil | | Woodstown Sandy Loam Soil | | | | | | | | | |
| | Compound 2 | | Compound 5 | | Compound 6 | | Compound 7 | | Compound 9 | | Compound 10 | |
| Rate kg/ha | 0.03 | 0.12 | 0.03 | 0.12 | 0.03 | 0.12 | 0.03 | 0.12 | 0.03 | 0.12 | 0.03 | 0.12 |
| Crabgrass | 0 | 0 | 0 | 3G | 2G | 7G | 4G | 8G,3C | 0 | 5G | 0 | 0 |
| Barnyardgrass | 3G | 4G | 0 | 5G,3H | 4G,3H | 8G,5H | 4G | 9G,5H | 0 | 0 | 0 | 0 |
| Sorghum | — | — | — | — | — | — | — | — | — | — | — | — |
| Wild Oats | 0 | 0 | 0 | 7G,8C | 5G,3H | 8G,8C | 4G | 8G,5H | 0 | 0 | 0 | 0 |
| Johnsongrass | 0 | 3G | 0 | 8H,3H | 8G,5H | 9G,8C | 7G,3H | 8G,3H | 0 | 0 | 0 | 0 |
| Dallisgrass | 0 | 0 | 0 | 5G | 4G | 9G,8C | 0 | 6G,3U | 0 | 0 | 0 | 0 |
| Giant foxtail | 0 | 2G | 0 | 2H | 5G,3H | 10C | 6G,3H | 8G,3H | 0 | 0 | 0 | 0 |
| Ky. bluegrass | 0 | 8G,5C | 4G | 10C | 10C | 10C | 10C | 10C | 0 | 5G | 0 | 0 |
| Cheatgrass | 0 | 0 | 0 | 10C | 6C,3H | 10C | 8G,9C | 10C | 0 | 0 | 0 | 0 |
| Sugarbeets | 3G | 6G,3H | 0 | 8G,7C | 8G,8C | 10C | 8G,7C | 10C | 9G,9C | 10C | 10C | 10C |
| Corn | 0 | 2G | 0 | 10C | 9G,9C | 10C | 5G,3H | 8G,8C | 0 | 7G,5H | 0 | 7G,5H |
| Mustard | 3G | 8G,8C | 8G | 9G,9C | 10C | 10C | 9G,9C | 10C | 10C | 10C | 9G,9C | 10C |
| Cocklebur | 0 | 0 | 0 | 6G | 5G | 5G,3H | 4G | 6G,2C | 4G | 3G | 5G | 5G |
| Pigweed | 0 | 8C | 0 | 3G | 10C | 10C | 9G,9C | 10C | 9G,8C | 10C | 10C | 10C |
| Nutsedge | 0 | 2G | 5G | 10E | 10E | 10E | 10E | 10E | 4G | 5G | 5G | 7G |
| Cotton | 0 | 0 | 0 | 7G,5H | 7G,5H | 8G,5H | 7G,5H | 8G,5H | 7G,3H | 8G,5H | 7G,5H | — |
| Morningglory | 0 | 3G,2C | 0 | 6G,3H | 8G,5H | 9G,7C | 7G,3H | 8G,5H | 8G,5H | 9G,8C | 8G,8C | 9G,7C |
| Cassia | 0 | 0 | 3G | 7G,3H | 7G | 9G,8C | 8G,3H | 9G,5C | 8G,3H | 9G,8C | 7G,3H | 9G,8C |
| Teaweed | 0 | 2C | 0 | 2G | 5G,3H | 7C,3H | 4G | 7G,3H | 4G | 8G,8C | 0 | 7G,5H |
| Velvetleaf | 0 | 2C,3G | 4G,3H | 8G,5H | 7G,5H | 8G,7C | 6G | 7G,8C | 8G,5H | 8G,5H | 0 | 3G |
| Jimsonweed | 0 | 4G | 0 | 4G | 7G,3H | 8G,7C | 6G | 7G,4C | 5G,3H | 9G,8C | 0 | 7G |
| Soybean | 0 | 2G | 0 | 0 | 6G,5H | 8G,5H | 5G | 8G,5H | 5G,5H | 8G,5H | 7G,5H | 9G,8C |
| Rice | 3G | 5G | 6G | 10E | 10E | 10E | 10E | 10E | 0 | 5G | 0 | 7G,3H |
| Wheat | 0 | 2G | 0 | 4G | 2G | 8G,8C | 3G | 6G | 0 | 0 | 0 | 0 |

Test C

Two ten-inch in diameter plastic pans lined with polyethylene liners were filled with prepared Fallsing-

TABLE C

| | Compound 8 | | | | Compound 9 | | | | Compound 10 | | | |
|---|---|---|---|---|---|---|---|---|---|---|---|---|
| | Pre-emergence | | Post-emergence | | Pre-emergence | | Post-emergence | | Pre-emergence | | Post-emergence | |
| Rate kg/ha | 0.01 | 0.03 | 0.01 | 0.03 | 0.01 | 0.03 | 0.01 | 0.03 | 0.01 | 0.03 | 0.01 | 0.03 |
| wheat | 0 | 0 | 0 | 2G | 0 | 0 | 0 | 0 | 0 | 0 | 0 | 0 |
| barley | 0 | 0 | 0 | 3G | 0 | 0 | 0 | 0 | 0 | 0 | 0 | 0 |
| wild oats | 0 | 0 | 0 | 3G | 0 | 3G | 0 | 0 | 0 | 2G | 0 | 0 |
| downy brome | 0 | 3G | 6G | 5G | 1C,2G | 1C,7G | 4G | 4G | 2G | 6G | 0 | 3G |

TABLE C-continued

| | Compound 8 | | | | Compound 9 | | | | Compound 10 | | | |
|---|---|---|---|---|---|---|---|---|---|---|---|---|
| | Pre-emergence | | Post-emergence | | Pre-emergence | | Post-emergence | | Pre-emergence | | Post-emergence | |
| Rate kg/ha | 0.01 | 0.03 | 0.01 | 0.03 | 0.01 | 0.03 | 0.01 | 0.03 | 0.01 | 0.03 | 0.01 | 0.03 |
| cheatgrass | 0 | 3G | 7G | 5G | 4G | 1C,8G | 5G | 5G | 0 | 4G | 0 | 3G |
| blackgrass | 0 | 0 | 3G | 4G | 6G | 1C,7G | 5G | 5G | 6G | 7G | 0 | 3G |
| annual bluegrass | 0 | 2G | 0 | 8G | 3G | 6G | 6G | 7G | 5G | 6G | 0 | 2G |
| green foxtail | 0 | 1C | 0 | 8G | 3G | 2G | 0 | 4G | 2G | 3G | 0 | 0 |
| quackgrass | 0 | 0 | 0 | 6G | 2G | 5G | 0 | 0 | 4G | 4G | 0 | 0 |
| Italian ryegrass | 0 | 0 | 0 | 7G | 3G | 2C,6G | 0 | 0 | 4G | 6G | 0 | 4G |
| ripgut brome | 0 | 0 | 0 | 7G | 0 | 2C,4G | 0 | 0 | 4G | 6G | 0 | 4G |
| Russian thistle | 0 | 0 | 4C | 4G | 0 | 2C,6G | 10C | 10C | 1C | 1C,4G | 10C | 10C |
| tansy mustard | 0 | 0 | 4G | 8G | 9G | 10C | 10C | 10C | 9G | 10C | 9G | 10C |
| *Galium aparine* | — | — | 2G | 10C | — | — | 4G | 5G | — | — | 7G | 10C |
| tumble mustard | 0 | 0 | 5G | 10C | 3C,9G | 10C | 10C | 10C | 2C,9G | 10C | 10C | 10C |
| kochia | 0 | 0 | 6G | 7G | 6G | 10C | 6G | 7G | 6G | 8G | 0 | 2G |
| shepherd's purse | 0 | 0 | — | — | 9G | 10C | 10C | 10C | 9G | 10C | 9G | 10C |
| *Matricaria inodora* | 0 | 0 | 8C | 10C | 6G | 7C,9G | 10C | 10C | 9G | 9G | 9C | 10C |
| black nightshade | 0 | 1C,2C | 3G | — | 8G | 8G | 0 | 5G | 2C,8G | 8G | 0 | 3G |
| yellow rocket | 0 | 0 | — | — | 2G | 10C | — | — | 4G | 6G | 2G | 4G |
| wild mustard | 0 | 0 | 6G | 7G | 7G | 10C | 10C | 10C | 6G | 8G | 8C,9G | 9C,9G |
| wild buckwheat | 0 | 0 | 5C,7G | 4C,7G | 7G | 8G | 9C,9G | 9C,9G | 5G | 8G | 8C,9G | 9C,9G |

Test D

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table D.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and rape. All plants were sprayed approximately 14 days after planting. Additional plant species such as bindweed and johnsongrass are sometimes added to this test.

It will be seen that the compounds tested are highly active post-emergence herbicides. Wheat is relatively tolerant.

TABLE D

| | Over-the-Top Soil/Foliage Treatment | | | |
|---|---|---|---|---|
| | Compound 6 | | Compound 7 | |
| Rate kg/ha | 0.015 | 0.06 | 0.015 | 0.06 |
| Soybeans | 9G,4C | 9G,2C | 10G,4C | 10G,4C |
| Velvetleaf | 10C | 10C | 9G,4C | 9G,5C |
| Sesbania | 10C | 10C | 8G | 9G,3C |
| Sicklepod | 10G,4C | 10C | 10G,3C | 10G,3C |
| Cotton | 9G,4C | 9G,2C | 10C | 9G,9C |
| Morningglory | 8G | 9G,6C | 8G,2C | 9G,8C |
| Alfalfa | 7G,6C | 10C | 6G | 9G,7C |
| Jimsonweed | 7G,2C | 7G,2C | 6G | 9G |
| Cocklebur | 5G | 8G | 2G | 8G |
| Corn | 7G | 8G,8U | 7G | 7G,6C |
| Crabgrass | 7G | 8G,6C | 2G | 2G |
| Rice | 6G,6C | 9G,7C | 6G,2C | 7G,2C |
| Nutsedge | 5G | 7G | 4G | 10C |
| Barnyardgrass | 8G | 10C | 4G,2H | 8G,8C |
| Wheat | 4G | 8G,6C | 4G | 4G |
| Giant foxtail | 5G | 9G,4C | 8G | 5G |
| Wild Oats | 4G | 6G,6C | 0 | 2G |
| Sorghum | 7G,6C | 8G,6C | 6G | 4G,4C |
| Rape | 10C | 10C | 9G | 9G,9C |
| Sugar beets | 8G | 9G | 7G | 7G |
| Johnsongrass | 8G,7U | 9G,7U | 6G | 7G,4C |
| Sunflower | 9G,6C | 6G | 2G | 6G |
| Bindweed | 3G | 8G | 0 | 0 |

What is claimed is:

1. A compound selected from

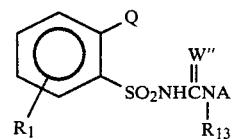

where
Q is

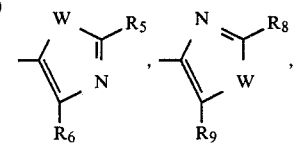

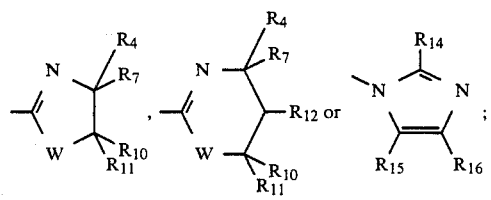

W" is O or S;
W is O, S, or NR:
R is H or $C_1-C_4$ alkyl;
$R_1$ is H, F, Cl, Br, $CH_3$, $CF_3$ or $OCH_3$;

$R_5$ is H, CH$_3$, C$_2$H$_5$, OCH$_3$, OC$_2$H$_5$, SCH$_3$, Cl or Br;
$R_6$ is H, CH$_3$ or C$_2$H$_5$;
$R_8$ is H, CH$_3$, C$_2$H$_5$, OCH$_3$, OC$_2$H$_5$, SCH$_3$, Cl or Br;
$R_9$ is H, CH$_3$ or C$_2$H$_5$;
$R_4$, $R_7$, $R_{10}$ and $R_{11}$ are independently H or C$_1$-C$_4$ alkyl;
$R_{12}$ is H or CH$_3$;
$R_{13}$ is H or CH$_3$;
$R_{14}$ is H, CH$_3$, C$_2$H$_5$, Cl, Br, CH$_3$O, C$_2$H$_5$O or CH$_3$S;
$R_{15}$ is H, CH$_3$ or C$_2$H$_5$;
$R_{16}$ is H, CH$_3$ or C$_2$H$_5$;
A is

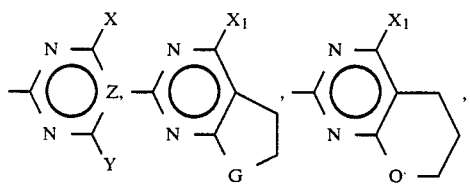

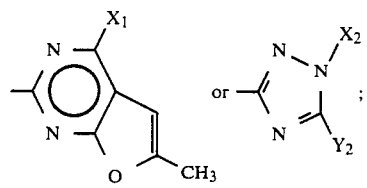

X is CH$_3$, OCH$_3$ or Cl;
Y is CH$_3$, C$_2$H$_5$, CH$_2$OCH$_3$, OCH$_3$, OC$_2$H$_5$, CH(OCH$_3$)$_2$, NH$_2$, NHCH$_3$, N(CH$_3$)$_2$, OCH$_2$CH$_2$OCH$_3$, OCH$_2$CF$_3$, CF$_3$, SCH$_3$, or

Z is CH;
X$_1$ is CH$_3$, OCH$_3$ or Cl;
G is O or CH$_2$;
X$_2$ is C$_1$-C$_3$ alkyl or CH$_2$CF$_3$;
Y$_2$ is CH$_3$O, C$_2$H$_5$O, CH$_3$S or C$_2$H$_5$S;
and their agriculturally suitable salts; provided that
(a) when R$_8$ is other than H, CH$_3$, C$_2$H$_5$ or SCH$_3$, then W is S or O;
(b) the total number of carbon atoms of R$_4$, R$_7$, R$_{10}$ and R$_{11}$ is less than or equal to 4;
(c) when X is Cl, then Y is OCH$_3$, OC$_2$H$_5$, NH$_2$, NHCH$_3$ or N(CH$_3$)$_2$;
(d) when Q is

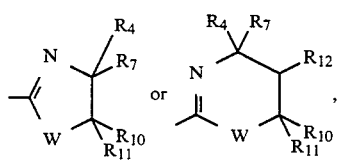

then R$_{13}$ is H, R is other than H, X is Cl or OCH$_3$ and Y is OCH$_3$ or OC$_2$H$_5$; and
(e) when W'' is S, then R$_{13}$ is H;
Q is

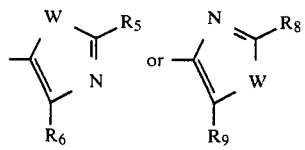

A is

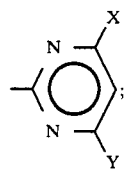

and
Y is CH$_3$, OCH$_3$, C$_2$H$_5$, OC$_2$H$_5$, CH$_2$OCH$_3$, CH(OCH$_3$)$_2$ or

2. A compound of claim 1 where R$_4$, R$_7$, R$_{10}$ and R$_{11}$ are independently H or CH$_3$; and W'' is O.
3. A compound of claim 2 where R$_1$ and R$_{13}$ are H.
4. A compound of claim 3 where
Y is CH$_3$, OCH$_3$, OC$_2$H$_5$, CH$_2$OCH$_3$ or

A is

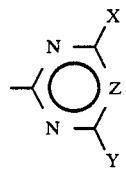

5. A compound of claim 4 where
Q is

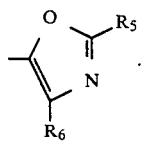

6. A compound of claim 4 where
Q is

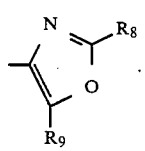

7. A compound of claim 4 where Q is

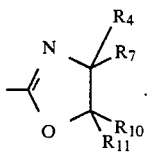

8. A compound of claim 4 where Q is

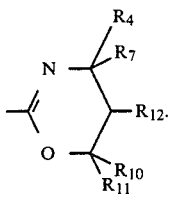

9. A compound of claim 4 where Q is

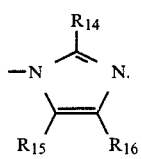

10. A compound of claim 4 where Q is

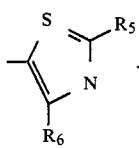

11. A compound of claim 4 where Q is

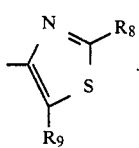

12. A compound of claim 4 where Q is

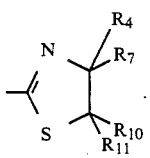

13. A compound of claim 4 where Q is

14. A compound of claim 4 where Q is

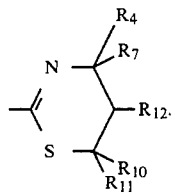

15. A compound of claim 4 where Q is

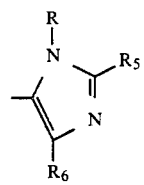

16. A compound of claim 4 where Q is

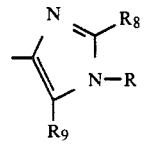

17. A compound of claim 4 where Q is

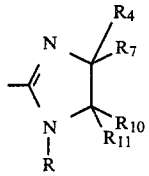

18. The compound of claim 1 N-[(4,6-dimethoxypyrimidin-2-yl)aminocarbonyl]-2-(4-oxazolyl)benzenesulfonamide.

19. The compound of claim 1 N-[(4,6-dimethylpyrimidin-2-yl)aminocarbonyl]-3-(2-ethyl-4-oxazolyl)-benzenesulfonamide.

20. A composition suitable for controlling the growth of undesired vegetation which comprises an effective amount of a compound of claim 1 and at least one of the following: surfactant, solid or liquid diluent.

21. A composition suitable for controlling the growth of undesired vegetation which comprises an effective amount of a compound of claim 2 and at least one of the following: surfactant, solid or liquid diluent.

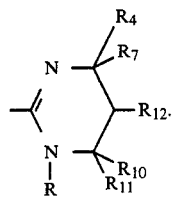

22. A composition suitable for controlling the growth of undesired vegetation which comprises an effective amount of a compound of claim 3 and at least one of the following: surfactant, solid or liquid diluent.

23. A composition suitable for controlling the growth of undesired vegetation which comprises an effective amount of a compound of claim 4 and at least one of the following: surfactant, solid or liquid diluent.

24. A composition suitable for controlling the growth of undesired vegetation which comprises an effective amount of a compound of claim 5 and at least one of the following: surfactant, solid or liquid diluent.

25. A composition suitable for controlling the growth of undesired vegetation which comprises an effective amount of a compound of claim 6 and at least one of the following: surfactant, solid or liquid diluent.

26. A method for controlling the growth of undesired vegetation which comprises applying to the locus to be protected an effective amount of a compound of claim 1.

27. A method for controlling the growth of undesired vegetation which comprises applying to the locus to be protected an effective amount of a compound of claim 2.

28. A method for controlling the growth of undesired vegetation which comprises applying to the locus to be protected an effective amount of a compound of claim 3.

29. A method for controlling the growth of undesired vegetation which comprises applying to the locus to be protected an effective amount of a compound of claim 4.

30. A method for controlling the growth of undesired vegetation which comprises applying to the locus to be protected an effective amount of a compound of claim 5.

31. A method for controlling the growth of undesired vegetation which comprises applying to the locus to be protected an effective amount of a compound of claim 6.

* * * * *